(12) United States Patent
Farthing et al.

(10) Patent No.: US 8,609,360 B2
(45) Date of Patent: *Dec. 17, 2013

(54) METHOD FOR DIAGNOSING ACUTE ISCHEMIC EVENTS IN HUMAN SUBJECTS

(71) Applicant: Virginia Commonwealth University, Richmond, VA (US)

(72) Inventors: Don Farthing, Chester, VA (US); Lei Xi, Richmond, VA (US); H. Thomas Karnes, Richmond, VA (US); Domenic Sica, Richmond, VA (US); Todd Gehr, Manakin-Sabot, VA (US); Lynne Gehr, Manakin-Sabot, VA (US); Martin Unverdorben, Pottstown, PA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/688,673

(22) Filed: Nov. 29, 2012

(65) Prior Publication Data

US 2013/0089880 A1 Apr. 11, 2013

Related U.S. Application Data

(63) Continuation of application No. 12/671,912, filed as application No. PCT/US2008/071929 on Aug. 1, 2008, now Pat. No. 8,343,731.

(60) Provisional application No. 60/024,659, filed on Jan. 30, 2008, provisional application No. 61/953,719, filed on Aug. 3, 2007.

(51) Int. Cl.
 *C12Q 1/26* (2006.01)

(52) U.S. Cl.
 USPC .......................................................... 435/25

(58) Field of Classification Search
 USPC .......................................................... 435/25
 See application file for complete search history.

(56) References Cited

U.S. PATENT DOCUMENTS

| | | | |
|---|---|---|---|
| 6,255,063 B1 | 7/2001 | Small et al. | |
| 8,343,731 B2 * | 1/2013 | Farthing et al. | 435/25 |
| 2003/0215952 A1 | 11/2003 | Bar-Or et al. | |
| 2005/0202521 A1 | 9/2005 | Crum | |
| 2012/0058099 A1 * | 3/2012 | Irwin | 424/94.4 |

OTHER PUBLICATIONS

Edited by G. Ali Qureshi Oxidative Stress and Neurodegenerative Disorders, Mar. 22, 2007, pp. 314-368 Chapter entitled Oxidative Stress in Stroke.*

Aygul R. et al. Plasma Oxidants and Antioxidants in Acute Ischaemic Stroke. J of International Medical Research 34(4)413-8, Jul.-Aug. 2006.*

Khan F. et al. Allopurinol Treatment Reduces Arterial Wave Reflection in Stroke Survivors. Cardiovascular Therapeutics 26(4)247-52, Nov. 2008.*

Mei et al. "Simultaneous Determination of Adenosine, Inosine, Hypoxanthine, Xanthine, and Uric Acid in Microdialysis Samples Using Microbore Column-High Performance Liquid Chromatography with a Diode Array Detector"; 1996; vol. 238, pp. 34-39. Abstract.

Castell et al. "Granule Localization of Glutaminase in Human Neutrophils and the Consequence of Glutamine Utilization for Neutrophil Activity" 2004; vol. 279, pp. 13305-13310 p. 13306, para 7.

Farthing D. et al. An HPLC.Method for Determination of Inosine and Hypoxanthine . . . J of Chromatography B 854(1-2)158-164, Jun. 25, 2007.

Jabs C. et al. Adenosine, Inosine, and Hypoxanthine/Xanthine . . . Clinical Chemistry 36(1)81-87, 1990.

Kather H. et al. Chemiluminescent Determination of Adenosine, Inosine, and Hypoxanthine/Xanthine. Analytical Biochemistry 163(1)45-51, May 15, 1987.

Mei D. 1996. et al. Simultaneous Determination of Adenosine, Inosine, Hypoxanthine, Xanthine . . . Analytical Biochemistry 238:34-39, 1996.

Lim Y. Role of Xanthine Oxidase in Reperfusion Injury in Ischemic Myocardium. The Seoul J of Medicine 29(2)131-142, Jun. 1988.

Kuwano K. Xanthine-Xanthine Oxidase Play an Important Role in the Progression of Acute Ischemic Heart Disease Syndromes. Kurume Igakkai 56(1)731-742, 1993.

Hlavay J. et al. Fibre Optic Biosensor for Hyopxanthine and Xanthine Based on a Chemiluminescence Reaction. Biosensors & Bioelectronics 9(3)189-195, 1994.

* cited by examiner

*Primary Examiner* — Ralph Gitomer
(74) *Attorney, Agent, or Firm* — Whitham Curtis Christofferson & Cook, PC

(57) ABSTRACT

Chemiluminescent of metabolic by-products of inosine and hypoxanthine is used to diagnose acute ischemic events in human subjects.

14 Claims, 23 Drawing Sheets

| OPTIMA | | TESTNAME: | XO (WELL MODE) | | 2007/11/17 13:16:17 | | |
|---|---|---|---|---|---|---|---|
| BMG LABTECH | | ID 1,2,3: | XO (WELL MODE) Luminescence 11/17/2007, 1:16:13 PM | | | | |
| Luminescence, well mode | | | Kinetic window | 1 | 2 | 3 | 4 |
| Plate type: COSTAR 96 | | | No. of intervals | 112 | - | - | - |
| | | | Kin. interval time [s] | 2.00 | - | - | - |
| | | | Meas. start time [s] | 0.0 | - | - | - |
| | | | Meas. interval time [s] | 1.00 | - | - | - |
| Gain: 3900 | | | To allow comparision of different kinetic windows all measurement values are normalized to 1 sec. | | | | |
| Emission filter: lens | | | | | | | |
| Required value [%]: 0 | | | Volume group | 1 | 2 | 3 | 4 |
| | | | Volume [μl] | 20 | - | - | - |
| | | | Used pump | 1 | - | - | - |
| Positioning delay [s]: 0.2 | | | Pump speed [μl/s] | 310 | - | - | - |
| Shaking width [mm]: 1 | | | Smart dispensing used | X | - | - | - |
| Shaking mode: orbital | | | Pump syringe vol. [ml] | 0.5 | - | - | - |
| Additional shaking: 2s before plate reading | | | Injection start time [s] | 120.0 | - | - | - |
| | | | Shaking after inject. [s] | 92 | - | - | - |
| | | | Target temperature [°C]: 25 | | | | |
| Reading directions: 3 None | | | Calculation Start1: 55 Stop1: 59      Start2: 60 Stop: 76 | | | | |
| Comment: | | | | | | | |
| Software version control: 2.10 R2 Software version evaluation: 2.10 R2 B:0004 Serial number: 413-3190 User: USER | | | | | | | |
| Audit trail | Saturday, November 17, 2007 - 2:03:28 PM, User 'USER': Data record created by performing test protocol 'XO (WELL MODE)' (started: Saturday, November 17, 2007 - 1:16:17 PM) using reader 413-3190. Saturday, November 17, 2007 - 2:03:40 PM, User 'USER': Automatic initialization of evaluation settings done during first opening of test run. Saturday, November 17, 2007 - 2:37:39 PM, User 'USER': Settings have been changed. Saturday, November 17, 2007 - 2:52:19 PM, User 'USER': Settings have been changed. Monday, December, 2007 - 7:57:52 AM, User 'USER': Settings have been changed. | | | | | | |
| Signatures | | | | | | | |

*Figure 9*

| OPTIMA | Testname: | XO (WELL MODE) | 2007/12/15 13:57:07 | ☐ Hide protocol settings |
| BMG LABTECH | ID 1,2,3: | XO (WELL MODE) Luminescence 12/15/2007, 1:57:03 PM | | 338.dbf |

| Luminescence, well mode | Kinetic window | 1 | 2 | 3 | 4 |
|---|---|---|---|---|---|
| Microplate: COSTAR 96 | No. of intervals | 112 | - | - | - |
| | Kin. interval time [s] | 2.00 | - | - | - |
| | Meas. start time [s] | 0.0 | - | - | - |
| | Meas. interval time [s] | 1.00 | - | - | - |

| No. | Emission | Gain | Volume group | 1 | 2 | 3 | 4 |
|---|---|---|---|---|---|---|---|
| 1 | lens | 3900 | Volume [μl] | 20 | - | - | - |
| | | | Injection start time [s] | 120.0 | - | - | - |
| | | | Shaking after inject. [s] | 92 | - | - | - |

Pos. delay [s]: 0.2  Additional shaking: 2s before plate reading
Reading direct: 3  Calculation Start1: 50  Stop1: 58   Start2: 59  Stop2: 112

Comment:

Calculation: Maximum  Chromatic  Table content
Table 1  Range1  1  Raw data

| | 1 | 2 | 3 | 4 | 5 | 6 | 7 | 8 | 9 | 10 | 11 | 12 |
|---|---|---|---|---|---|---|---|---|---|---|---|---|
| A | | | | | | | | | | | | |
| B | | | | | 2451 | 2592 | | | | | | |
| C | | | | | | | | | | | | |
| D | | | | | | | | | | | | |
| E | | | | | | | | | | | | |
| F | | | | | | | | | | | | |
| G | | | | | | | | | | | | |
| H | | | | | | | | | | | | |

Table 2  Range2  1  Raw data

| | 1 | 2 | 3 | 4 | 5 | 6 | 7 | 8 | 9 | 10 | 11 | 12 |
|---|---|---|---|---|---|---|---|---|---|---|---|---|
| A | | | | | | | | | | | | |
| B | | | | | 145018 | 150265 | | | | | | |
| C | | | | | | | | | | | | |
| D | | | | | | | | | | | | |
| E | | | | | | | | | | | | |
| F | | | | | | | | | | | | |
| G | | | | | | | | | | | | |
| H | | | | | | | | | | | | |

Table 3
Table calculation: Table2 - Table1

| | 1 | 2 | 3 | 4 | 5 | 6 | 7 | 8 | 9 | 10 | 11 | 12 |
|---|---|---|---|---|---|---|---|---|---|---|---|---|
| A | | | | | | | | | | | | |
| B | | | | | 142567 | 147673 | | | | | | |
| C | | | | | | | | | | | | |
| D | | | | | | | | | | | | |
| E | | | | | | | | | | | | |
| F | | | | | | | | | | | | |
| G | | | | | | | | | | | | |
| H | | | | | | | | | | | | |

*Figure 11*

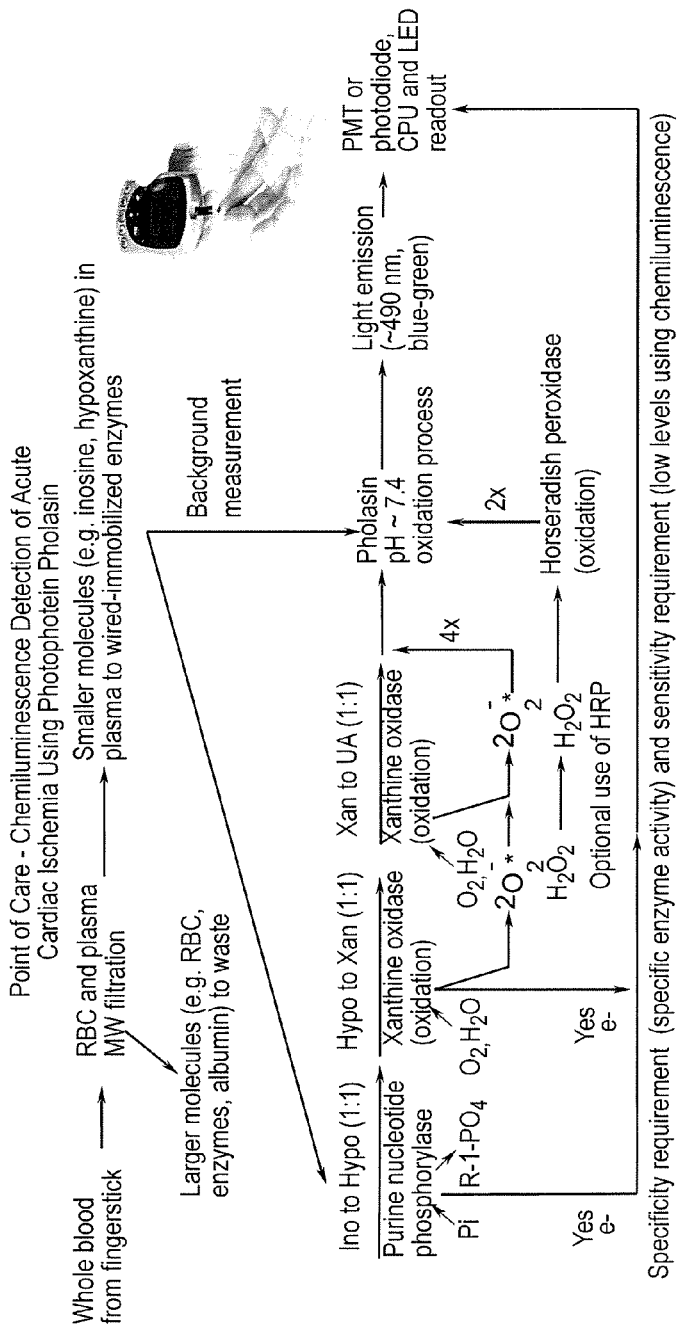
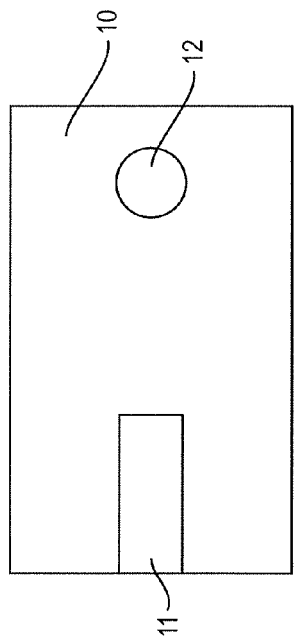
*Figure 23A*
*Figure 23B*

METHOD FOR DIAGNOSING ACUTE ISCHEMIC EVENTS IN HUMAN SUBJECTS

CROSS-REFERENCE TO RELATED APPLICATIONS

This application is a continuation application of U.S. Ser. No. 12/671,912, filed Mar. 14, 2011, now U.S. Pat. No. 8,343,731, which itself is a National Stage 371 application of PCT/US2008/071929 filed Aug. 1, 2008, which claims priority to U.S. Provisional Application 60/024,659 filed Jan. 30, 2008 and U.S. Provisional Application 61/953,719 filed Aug. 3, 2007

BACKGROUND OF THE INVENTION

1. Field of the Invention

The invention generally relates to the early detection of ischemic events such as cardiac ischemia. In particular, the invention provides methods for detecting inosine and/or hypoxanthine, or metabolic by-products thereof, as early biomarkers of ischemia.

2. Background of the Invention

Cardiovascular diseases (e.g. acute myocardial infarction (MI)) are the leading cause of mortality in the world [Naudziunas et al., 2005; Okrainec et al., 2004; Domer et al., 2004, AHRQ, 2000]. Each year in the US, approximately 7-8 million patients present with non-traumatic chest pain and seek emergency medical treatment [Morrow et al., 2007]. Current emergency medical evaluation on these patients suspected of having acute MI includes obtaining patient history, signs and symptoms, vitals, electrocardiogram (ECG) and blood evaluation for specific cardiac biomarkers [Beyerle, 2002; A.D.A.M. Inc., 2005; Lees, 2000]. However, the percent diagnostic accuracy of acute MI when using patient signs and symptoms, ECG and c-troponin is only approximately 50%. With the addition of the recently FDA cleared albumin cobalt binding assay, the diagnostic accuracy improves to approximately 70%; hence the need for additional research for biomarkers of acute cardiac ischemia to further improve patient diagnostic accuracy is important.

The hospital emergency department blood evaluation determines levels of several specific endogenous cardiac protein biomarkers (e.g. cardiac troponin I and T (cTnI, cTnT), creatine kinase-MB (CK-MB) isoform, and myoglobin). However, these protein biomarkers are indicative of cardiac tissue necrosis, and are typically detected hours after the acute cardiac event (infarct), and not at the time of acute cardiac ischemia.

One recent published scientific editorial requested the need for early onset biomarkers of acute cardiac ischemia prior to cardiac tissue necrosis [Morrow et al., 2003]. Ideally, these early onset biomarkers would aid emergency medical services (EMS) personnel in the rapid diagnosis and treatment of initial acute cardiac ischemia (potentially acute MI), thus increasing the survival rate of acute MI victims every year. One research group [Bhagavan et al., 2003] addressing the scientific editorial request, describes a blood measurement for ischemia modified albumin (IMA), which appears at an elevated level in the bloodstream from patients undergoing an ischemic cardiac event; however the author's state that the colorimetric test would not discriminate between cardiac ischemic patients with and without acute MI (e.g. angina), and recent clinical evaluations of the test assay have reported significant false positive results.

This technology is described in U.S. Pat. No. 7,282,369 to Par-Or et al. (Oct. 16, 2007) which teaches rapid methods for the detection of ischemic states and kits for use in such methods. The methods are based on detecting and quantifying the existence of an alteration of the serum protein albumin which occurs following an ischemic event. Methods for detecting and quantifying this alteration include evaluating and quantifying the cobalt binding capacity of circulating albumin, analysis and measurement of the ability of serum albumin to bind exogenous cobalt, detection and measurement of the presence of endogenous copper in a purified albumin sample and use of an immunological assay specific to the altered form of serum albumin which occurs following an ischemic event. Also taught is the detection and measurement of an ischemic event by measuring albumin N-terminal derivatives that arise following an ischemic event, including truncated albumin species lacking one to four N-terminal amino acids or albumin with an acetylated N-terminal Asp residue.

U.S. Pat. No. 7,063,782 to Wayment et al (Jun. 20, 2006) teaches electrochemical methods and devices for in vitro detection of an ischemic event in a patient sample. Following addition of a known amount of a transition metal ion to the patient sample, electrodes are used to measure the current or potential difference of non-sequestered transition metal ion in the sample. The amount of non-sequestered transition metal ion in the sample reflects the degree of modification to albumin that is the result of an ischemic event. However, several clinical studies have reported the test to have significant false positive results.

There is an ongoing need to discover and develop methods for detecting early onset biomarkers of acute cardiac ischemia.

SUMMARY OF THE INVENTION

The present invention is based on the development of methods to rapidly diagnose whether a patient has or is experiencing an ischemic event by detecting metabolic by-products of xanthine oxidase (XO) activity in a biological sample from the patient. The method is especially useful in emergency situations where a correct diagnosis may be a matter of life or death, and must be made as quickly and accurately as possible. The methods provide medical practitioners (especially emergency medical personnel) with the ability to rapidly distinguish, for example, early cardiac ischemia from other possible causes of chest pain which have fewer serious immediate consequences (e.g. anxiety, heart burn, etc.), and thus fosters early, appropriate treatment of patients. In addition, the methods may be used to monitor, on an ongoing basis, cardiac patients or persons considered to be at risk of experiencing or undergoing an adverse ischemic event to insure early detection and intervention. In one embodiment, a chemiluminescent method is used to detect metabolic by-products of XO activity, for example, hydrogen peroxide ($H_2O_2$) and/or superoxide anion radicals. These products may be generated by the action of XO on the substrates hypoxanthine and/or xanthine.

BRIEF DESCRIPTION OF THE DRAWINGS

FIG. 9. BMG luminometer set points used for flash mode experiments.

FIG. 11. BMG spread sheet (Excel®) computations, method and data processing set points, and file name are documented for GLP compliance. Results are reported in spread sheet cells based on microplate sample well location (96 well plates).

FIG. 23A-B. Schematic of point of use hand held device. A, flow chart or procedure; B, schematic representation of device.

DETAILED DESCRIPTION

Figure 1:
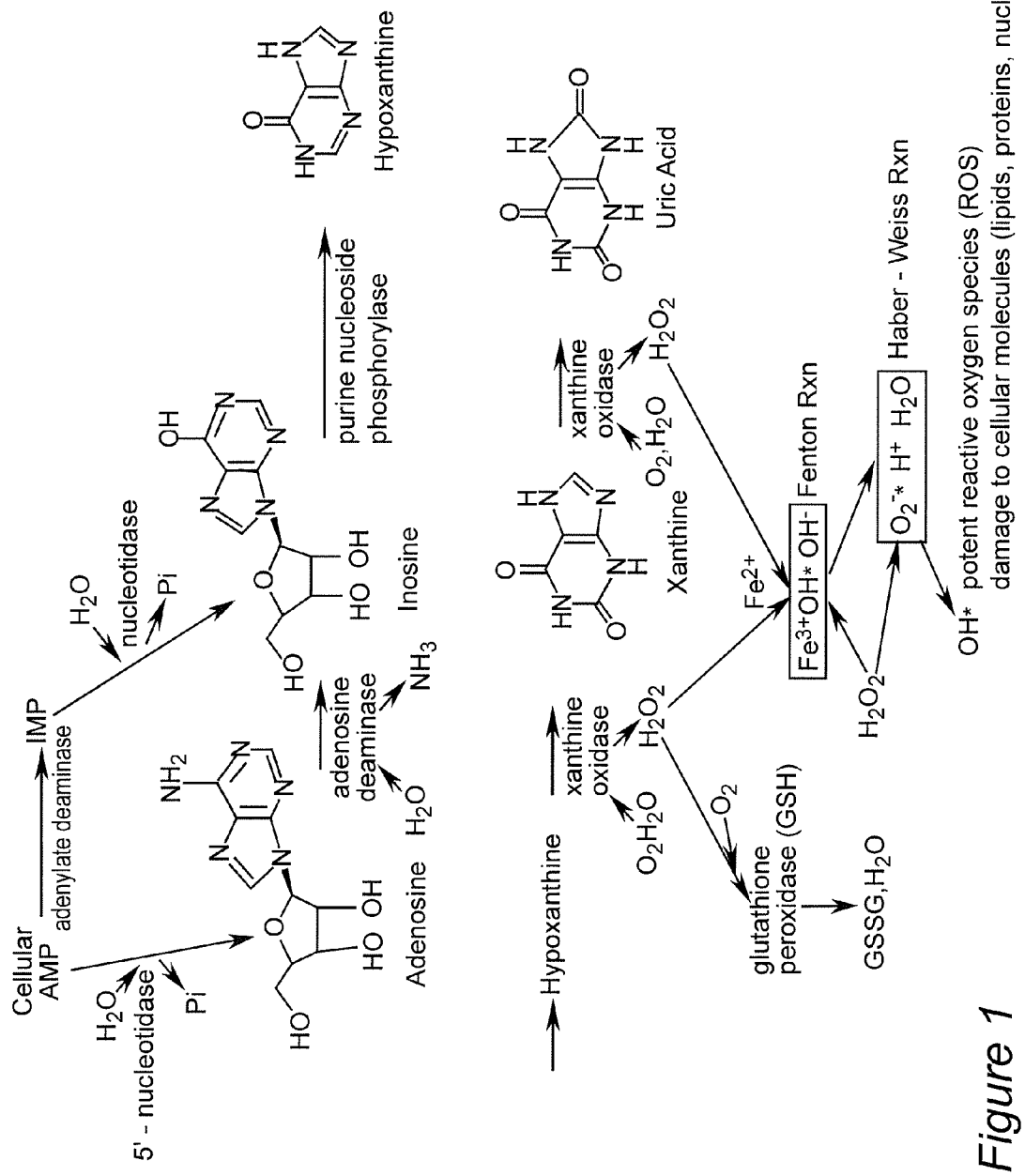
FIG. 1. Schematic drawing of cardiac cellular adenosine triphosphate (ATP) catabolism due to oxidative stress and potential oxygen reperfusion injury due to free radical generation.

The present invention is based on the development of methods to rapidly diagnose the occurrence of an ischemic event in a patient, by detecting, in a biological sample from the patient, the metabolic by-products (e.g. various reactive oxygen species, ROS) generated by the activity of the enzyme xanthine oxidase (XO). For example, the method is especially useful to rapidly distinguish, at an early stage, acute, cardiac ischemia from other possible conditions in a patient who is experiencing chest pain, thus allowing appropriate follow-up treatment. The method is particularly valuable in emergency situations where emergency personnel otherwise, when using less rapid and less reliable prior art methods, lose valuable time in diagnosing or even misdiagnosing conditions such as cardiac ischemia.

In one embodiment, the by-products that are detected are one or both of $H_2O_2$ and superoxide anion radical ($O^{2-}$, SAR). These by-products are typically generated by the action of XO on one or more of the substrates hypoxanthine and xanthine. XO converts hypoxanthine to xanthine and xanthine to uric acid, with concomitant generation of by-products $H_2O_2$ and SAR. The by-products may be generated by exposing a biological sample to XO. Alternatively, in some embodiments, the biological sample is first exposed to the enzyme purine nucleoside phosphorylase (PNP) in order to convert inosine in the sample to hypoxanthine Subsequent exposure of the sample to XO generates $H_2O_2$ and SAR. In the first embodiment, which does not utilized PNP, XO acts on endogenous hypoxanthine and xanthine (hypoxanthine and xanthine that are already present in the sample). In the second embodiment, XO acts on both the endogenous hypoxanthine and xanthine, as well as on the hypoxanthine that is produced by the action of PNP.

The biological samples that are obtained and tested according to the method may be any that contain elevated levels of inosine and/or xanthine and/or hypoxanthine as a result of ischemia and one or more or all of these substances may be measured. Examples of such biological samples include but are not limited to biological fluids such as blood, plasma, saliva, spinal or brain fluid, breath or aerosol samples, urine, etc.

The ischemic event that is detected may be or be due to a variety of conditions such as cardiac ischemia, stroke, stable and unstable angina, acute coronary syndrome, and other conditions that are known to be associated with ischemia.

In order to detect XO metabolic by-products, in some embodiments of the invention, chemiluminescent methods are used while in other embodiments of the invention, immunological methods are employed. Depending on the embodiment of the assay that is employed, the sensitivity of the assay is at least in the µM range, and may extend to the nM or even pM range for detecting the by-products.

Chemiluminescent Methods

In one embodiment of the invention, the methods involve the use of chemiluminescence to indirectly detect inosine and/or hypoxanthine by measuring the level of one or more metabolic by-products of inosine and/or hypoxanthine. By "metabolic by-products" we mean substances, compounds or other chemical entities that are produced during a chemical reaction in which inosine and/or hypoxanthine are enzyme substrates for the enzyme XO. Herein, "metabolic by-products" may also be referred to as "by-products of enzyme reactions", "metabolites", "by-products" or other similar terms or phrases that are recognized by those of skill in the art. In one embodiment, the metabolites are by-products of the catalysis of hypoxanthine by the enzyme xanthine oxidase (XO). In another embodiment, the metabolites are by-products of the catalysis of inosine and hypoxanthine by the enzymes purine nucleoside phosphorylase (PNP) and xanthine oxidase (XO). Biological enzymes PNP and XO are specific for enzymatic conversions of inosine and hypoxanthine, respectively. The PNP enzyme converts inosine to hypoxanthine and XO converts hypoxanthine to xanthine, followed by XO conversion of xanthine to final product uric acid (in human species). Each time XO reacts with one mole of hypoxanthine and with one mole of xanthine, the metabolic by-products of each XO enzymatic turnover is the production of one mole of hydrogen peroxide ($H_2O_2$) and two moles of superoxide anion radical ($O_2^-$). Both of these by-products can become substrates for luminescence (e.g. chemiluminescence) type reactions and the present invention is based on the development of rapid and accurate chemiluminescent assays that detect and measure the level (quantity, amount, etc.) of one or both of $H_2O_2$ and ($O_2^-$). The by-products may also be substrates for colorimetric, phosphorescent or fluorescent type reactions that allow for measurable detection.

In general, the methods of the invention involve obtaining a blood or plasma sample from a patient that is or has recently experienced chest pain. Typically, a blood sample is obtained using a suitable technique, many of which are known to those of skill in the art. For example, lithium heparin tubes are known and may be used. The plasma component of whole blood is separated, e.g. by centrifugation, filtration, etc. or other suitable methods. Typically, a molecular weight cutoff (MWCO) filter in the range of 5,000 to 50,000 is sufficient, with a range of 10,000 to 35,000 being preferable. Centrifugation at e.g. ~1000×g for about 1-10 minutes or less will usually be appropriate, and is well within the purview of one of skill in the art to determine. Suitable aliquots of the plasma sample are then treated according to the methods of the invention to convert inosine and hypoxanthine in the sample to species that are readily detected by chemiluminescence, as follows.

PNP Reaction

In this embodiment of the invention, aliquots of plasma are combined with PNP, e.g. the plasma may be transferred into a suitable reaction vessel and an appropriate quantity of PNP is then added to the reaction vessel, or plasma may be added to a reaction vessel that already contains PNP. In either case, the combining/mixing of the plasma and PNP is carried out under conditions that allow the PNP to convert inosine in the sample to hypoxanthine. Suitable reaction vessels include but are not limited to, for example, plates containing wells such as 96-well plates, various known glass and plastic test tubes, by spotting the reaction mixture onto a substrate, within various known hollow microfibers, etc. In a preferred embodiment, the reaction vessel is a 96-well plate. Generally, the volume of plasma that is utilized is in the range of from about 1 µl to about 200 µl, and preferably is about 20 µl. In addition, the plasma aliquot may be diluted as well, e.g. appropriate media may be in the reaction vessel and the plasma added to it, or added to the reaction vessel after the plasma had been added. Generally, the amount of dilution will be in the range of from about 0 to about 100-fold, or from about 0 to about 50 fold, or from about 0 to about 25-fold, or from about 0 to about 10-fold. Suitable dilution buffers include any that allow the enzyme reactions to proceed at a sufficient rate (e.g. at least about 10%, 20%, 30%, 40%, 50%, 60%, 70%, 80%, 90%, 100% or possibly even more) of the rate that is displayed under optimal standardized conditions, so as to achieve detectable amounts of product within the rapid time frame of the assay. At the same time, the buffers utilized in the assay must not interfere with the chemiluminescence that is generated e.g. they must permit at least about 10%, 20%, 30%, 40%, 50%, 60%, 70%, 80%, 90%, or even 100% of the maximal possible luminescence. Generally, these two objectives can be achieved by using buffers which buffer in a pH range of from about 7.0 to 8.0, or preferably from about 7.2 to about 7.8, and more preferably at or about pH 7.4. In other words, the buffers that are utilized buffer at or near physiological pH, as understood by those of skill in the art. Buffers of choice include but are not limited to, for example, various phosphate buffers (e.g. dibasic sodium phosphate, potassium phosphate, etc.); various Tris buffers that buffer at or near pH 7.4; Zwitterionic "Good's" buffers that buffer at or near pH 7.4; borate buffers; imidazole buffers, amino acid containing buffers (e.g. histidine), and others that will occur to those of skill in the art. In a preferred embodiment, the buffer is 20 mM dibasic sodium phosphate, pH 7.4.

As will be understood by those of skill in the art, to minimize experimental variability, each assay preferably is carried out at least in duplicate, possibly triplicate, or with even higher numbers of identical repetitive aliquots. PNP enzyme is added to each reaction to achieve a final concentration that is generally in the range of from about 100 to about 1000 mU/ml, or from about 200 to about 900 mU/ml, or from about 300 to about 700 mU/ml, typically from a standardized stock solution. Those of skill in the art will recognize that the amount of enzyme that is used may be varied and/or optimized depending on several factors (e.g. temperature, volume, method of detection, etc.). The PNP is incubated in the reaction vessel with the plasma under conditions that are favorable for quantitative conversion of inosine to hypoxanthine, e.g. at a constant temperature in the range of from about 20° C. to about 40° C., and preferably in the range of from about 25° C. to about 37° C., and most preferably at 25° C. or at 37° C. Generally, the incubation reaction is allowed to proceed for a time period in the range of from about 60 seconds to about 5 minutes or less. Conversion is typically complete after about 120 seconds of incubation. Although those of skill in the art will recognize that longer incubations may be used if desired, in the interest of reducing the time required for this rapid assay, while still achieving quantitative conversion of the substrates, a preferred reaction time is 120 seconds.

Alternatively, PNP may also be added to the sample during the centrifugation (plasma separation) step in order to further speed the procedure. For example, a sufficient quantity of PNP may be added directly to the blood sample before centrifugation; or PNP may be added to plasma before the plasma is transferred to the reaction vessel, or the sample tube used for collecting the blood sample may be coated or partially coated with PNP, etc. Any suitable strategy for combining the plasma sample with PNP or for contacting the sample with PNP may be used, so long as conditions are such that inosine in the plasma is substantially converted to hypoxanthine. Examples include but are not limited to immobilizing the enzyme on a substrate (e.g. beads, strips, etc.), or even spotting (placing or otherwise transferring) the sample onto a suitable substrate and exposing the substrate to a solution of enzyme, etc.

The PNP enzyme that is utilized may be from any suitable source. In some embodiments, the PNP is human PNP. In other embodiments, other sources are used, e.g. bacterial PNP.

XO Reaction

Thereafter, (i.e. preferably after about 120 seconds) a suitable quantity of XO enzyme is mixed with the reacted sample to effect the quantitative conversion of hypoxanthine to xanthine. In most embodiments, XO is added directly to the plasma/PNP mixture in the reaction vessel. However, as discussed above, in some embodiments, PNP is not used and the blood or plasma sample is contacted with XO to convert endogenous hypoxanthine and xanthine. XO enzyme is added to each reaction to achieve a final concentration that is generally in the range of from about 100 to about 1000 mU/ml, or from about 200 to about 900 mU/ml, or from about 300 to about 700 mU/ml. Those of skill in the art will recognize that the amount of enzyme that is used may be varied and/or optimized depending on several factors (e.g. temperature, volume, method of detection, etc.). The XO is incubated in the reaction vessel with the plasma under conditions that are favorable for quantitative conversion of hypoxanthine to xanthine and xanthine to uric acid, e.g. at a constant temperature in the range of from about 20° C. to about 40° C., and preferably in the range of from about 25° C. to about 37° C., and most preferably at 25° C. or at 37° C.

Generally, production of by-products begins immediately upon the addition of XO. Monitoring of the production of by-products may begin any time after addition of XO, and preferably immediately after, since the reaction is substantially over after about 30 seconds. The luminescent signal may be monitored throughout the reaction, or may be monitored at one or more selected time intervals.

Those of skill in the art will further understand that rather than "adding" XO to the sample, the sample may be contacted with XO by some other means, e.g. XO may be immobilized on beads, strips, or other substrates, etc., and the sample may be brought into contact with the enzyme by an appropriate means, e.g. dipping or spotting, etc. In addition, the sample may be spotted or otherwise located or placed onto a suitable substrate and the substrate may then be exposed to a solution of enzyme, etc. Further, in some embodiments, both PNP and XO may be co-located on a suitable substrate.

Chemiluminescent Measurement

As will be understood by those of skill in the art, the precise manner in which by-product measurement is carried out depends on which by-products ($H_2O_2$ or SAR, or both) are measured, and which reagent is used to detect the by-product(s). Detection reagents are typically added to the reaction mixture either together with or before the addition of XO and, as discussed above, the reaction is monitored immediately.

In one embodiment of the invention, SAR are detected. Since one mole of hypoxanthine generates 4 moles of superoxide anion radicals (SAR) as a by-product of XO activity, using a chemiluminescent material that reacts with SAR should theoretically provide more luminescence signal than would $H_2O_2$, potentially increasing the sensitivity two fold in comparison. Thus, when SARs are measured, very high sensitivity is achieved even at low concentrations or inosine and hypoxanthine in the blood sample. Examples of reagents that can be used in the detection of SAR include but are not limited to lucigenin (bis-N-methylacridinium); PHOLASIN®; and others that may occur to those of skill in the art. PHOLASIN® utilizes the highly sensitive bioluminescent photoprotein PHOLASIN® from the bivalve mollusc *Pholas dactylus*. In a preferred embodiment, PHOLASIN® is used.

However, in other embodiments of the invention, $H_2O_2$ may be detected. In this case, reagents including but not limited to horseradish peroxidase/lucigenin, horseradish peroxidase/luminol, etc. may be utilized. If using luminol or lucigenin as the luminescent material, the hydrogen peroxide (which has both oxidizing and reducing capabilities) reacts with the horseradish peroxidase (HRP) (or other peroxidase) enzyme to generate hydroxyl radical, which in turn reacts with luminol to generate measurable blue light ~450 nm. Thus an amplification of the signal (one mole of hypoxanthine and xanthine generates two moles of hydrogen peroxide) occurs. Preferably, the reaction is also carried out with signal enhancers.

Signal enhancers may be added to any of the luminescence reactions described herein to increase the detectable signal produced by reaction of the by-product with a chemiluminescent reagent. Examples of signal (sensitivity) enhancers include but are not limited to Adjuvant-K™ (which is specific for PHOLASIN®), and other that may occur to those of skill in the art. The use of an enhancer may be especially important since this is a rapid assay and does not generally require "clean-up" of the sample prior to analysis. Therefore, substances that interfere with the enzyme reactions or with the luminescent labeling or signal may still be in the sample. In other embodiments of the invention, some "clean-up" techniques may be employed, which include but are not limited to strong anion exchange (SAX) for removal of organic acids, other solid phase extractions (e.g. silica), the addition of base to salt out organic acids, various liquid/liquid extractions, etc.

In other embodiments of the invention, more than one by-product is detected. For example, both $H_2O_2$ and SARs may both be detected, either in the same reaction mixture, or in parallel side-by-side reactions, one of which measures $H_2O$, and the other of which measures SAR.

Typically, the chemiluminescent reagent's reaction with a by-product is detected at a characteristic wavelength, usually a wavelength at which the signal is maximal, or at which other substances in the reaction do not interfere significantly. Those of skill in the art are familiar with obtaining such measurements. Generally a suitable automated luminometer is utilized as described in Example 4 below, and any such means for measuring a suitable wavelength of light produced in proportion to the about of by-product(s) of interest may be used in the practice of the invention.

Time Required for Assay

The assay of the present invention is a rapid assay, i.e. it can generally be completed in about 10 minutes or less, after a blood sample is obtained from the patient. Those of skill in the art will realize that the time frame of the assay does not take into account transporting the sample to a lab where the analysis takes place, but assumes that the time begins one the blood sample is in the hand of a skilled professional, i.e. one who is trained to carry out the assay. Likewise, the end point of the assay is considered to be the time as which data can be read out from the instrument that is used to measure luminescence. In some embodiments of the invention, the time required for the assay is about 10 minutes or less, 9 minutes or less, 8 minutes or less, 7 minutes or less, 6 minutes or less, 5 minutes or less, 4 minutes or less, 3 minutes or less, 2 minutes or less, or even 1 minute or less.

Interpreting the Results

Those of skill in the art are familiar with the use of baselines or controls for determining the significance of a measurement, and with techniques for calibrating an instrument, and it is understood that such appropriate measures would be taken to ensure accuracy and reproducibility of the assay. Typically, measurement of a level of by-product in a patient sample that exceeds a 95%, 96%, 97%, 98%, 99% or even higher (e.g. 99.9%), and preferably a 99% or higher confidence interval threshold, when compared to normal controls, is considered to be a positive indicator of cardiac ischemia. The cutoff threshold is typically 4.6 µM combined concentration of inosine, xanthine, and hypoxanthine, which corresponds to a RLU reading in the range of about 180,000, depending on the instrument that is used to carry out the measurement and the calibration of the instrument. Those of skill in the art will recognize that RLU quantities may vary, depending on the instrument, its calibration, etc. Conversely, levels below this threshold indicate that the patient has not yet experienced cardiac ischemia. Such evaluations will typically be made by a skilled professional such as a physician, physician's assistant, trained emergency worker, etc. However, health care professionals will also usually prefer to repeat the test after a suitable length of time to confirm the initial finding. The test may be repeated one or more times, as necessary, until the health care professional is satisfied that a correct diagnosis has been made, and appropriate action has been taken.

Figure 20:
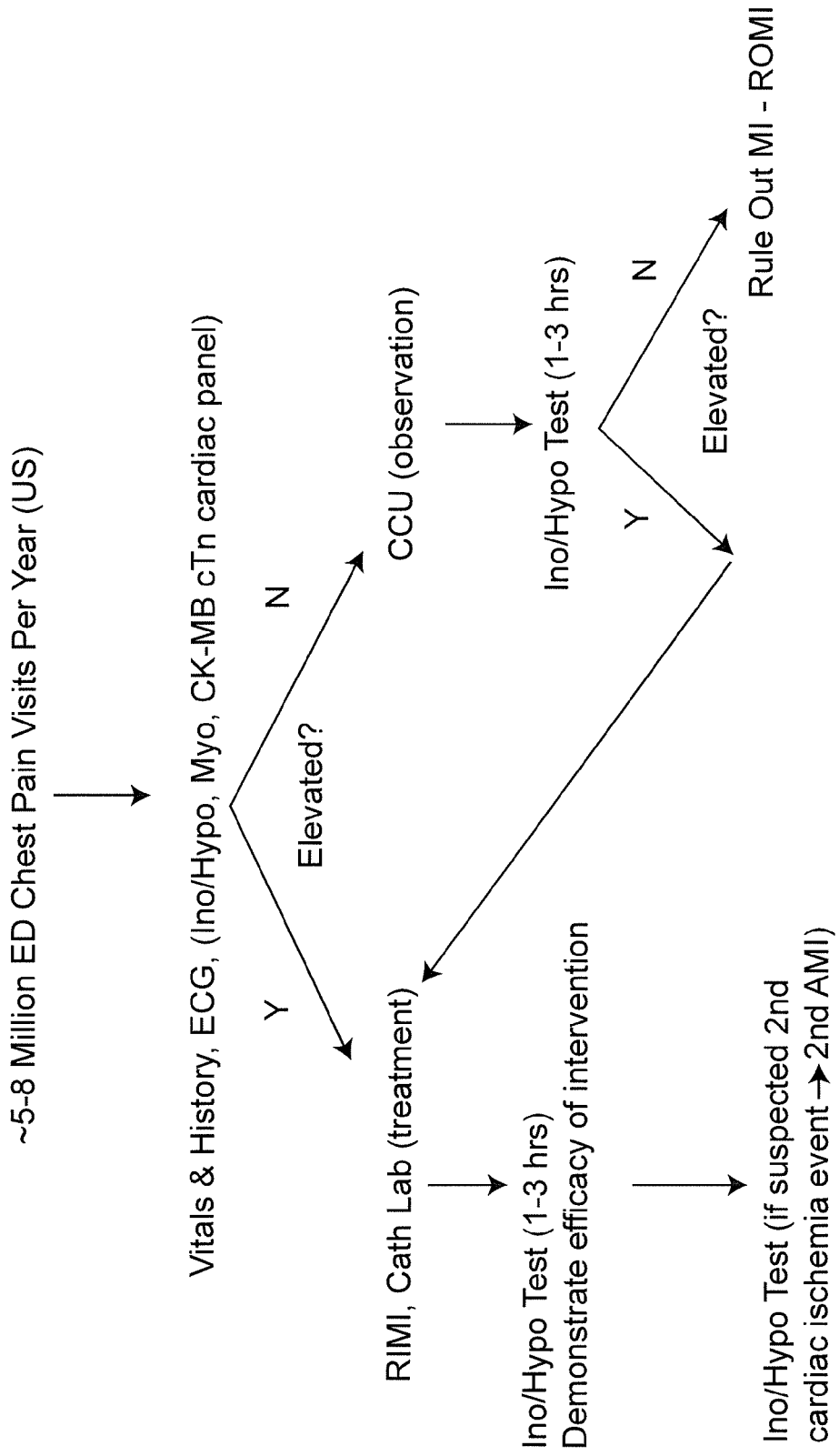
FIG. 20. Schematic representation of the assay integrated within the diagnosis of a cardiac ischemic event.

FIG. 20 depicts a representative scenario for intake procedures and triage of a patient that presents with chest pain, and Example 4 further discusses this aspect of the invention. In addition to taking vital signs and history, a panel of known cardiac tests are carried out, including the inosine and/or hypoxanthine test described herein. If the levels of inosine/hypoxanthine are elevated, appropriate intervention immediately ensues and the patient is treated as though cardiac ischemia is occurring, has occurred or is imminent. The inosine/hypoxanthine assay may be repeated later (e.g. after about 1-3 hours) to confirm the efficacy of intervention, and thereafter as necessary to insure proper treatment of the patient.

On the other hand, if the initial test indicates the inosine/hypoxanthine levels are not elevated, the patient may simply be observed and/or other tests may be carried out to determine if there is another cause of the chest pain. The inosine/hypoxanthine test may be repeated (e.g. after about 1-3 hours) in order to confirm the initial result, at which time a decision will again be made regarding whether or not cardiac ischemia is indicated. If yes, then appropriate treatment ensues. If not, then ischemia may be ruled out and an alternate suitable treatment protocol is prescribed.

2. Immunological Detection of Inosine and/or Hypoxanthine

In another embodiment of the invention, the method to detect inosine and/or hypoxanthine in immunological in nature and involves the use of antibodies specific for one or the other or both of inosine and hypoxanthine. In one embodiment of the invention, the antibodies are monoclonal antibodies. Immunoassay is a well established sensitive technique commonly used in clinical chemistry environments. This embodiment of the invention provides a sensitive immunoassay technique, which utilizes antibodies for detection of inosine and hypoxanthine levels in biological fluids (e.g. plasma, serum, whole blood). After development of the antibodies, several established quantitative techniques using antibodies may be utilized (e.g. Competitive Binding, FIG. 21; or a "Sandwich" Assay, FIG. 22).

For development of the antibodies, due to the small size of inosine and hypoxanthine (<300 Daltons molecular weight), these molecules must generally be conjugated to a carrier protein (e.g. albumin) to elicit an antibody response in the host animal (e.g. rabbit, goat, and mouse). The current established techniques for producing and isolating monoclonal antibodies are preferred over polyclonal antibodies, as this will ultimately increase the specificity of the testing assay. The produced antibodies can be tagged (fluorescent label) using current established labeling techniques.

Figure 21:
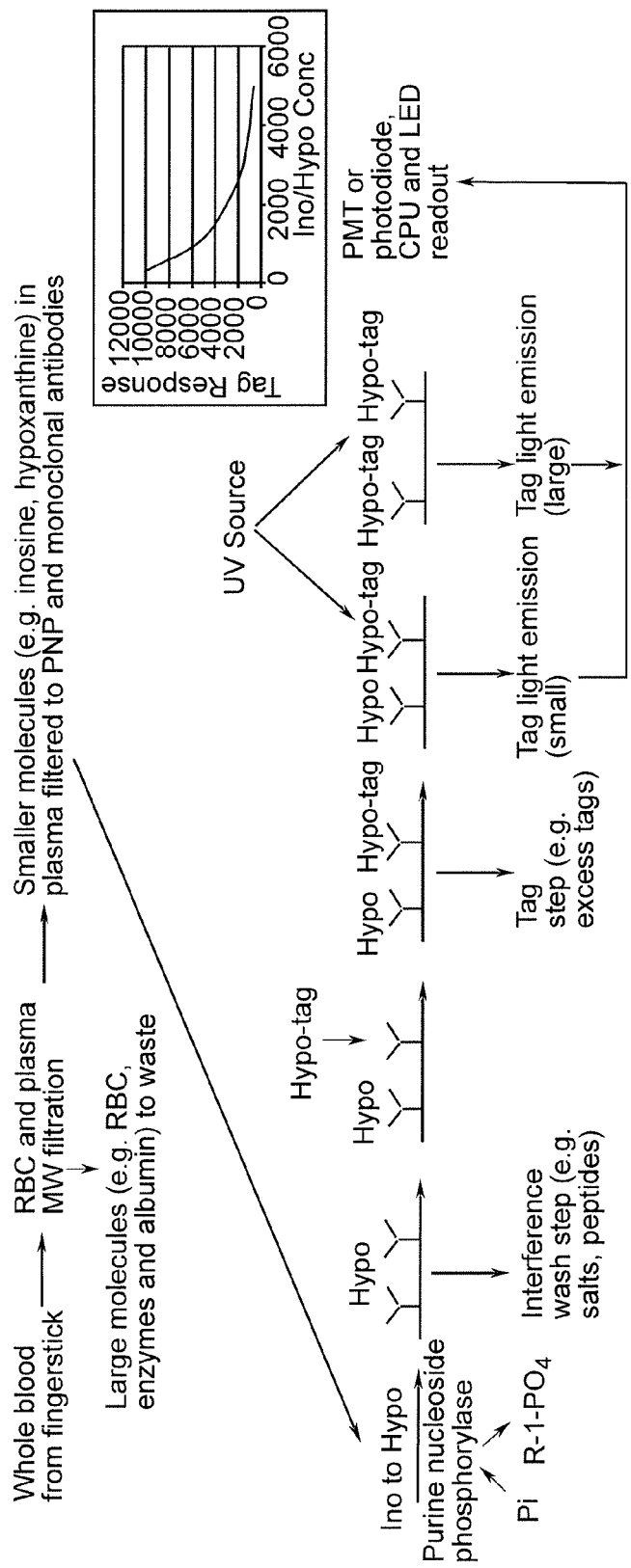
FIG. 21. Schematic of competitive binding immunoassay.
Figure 22:
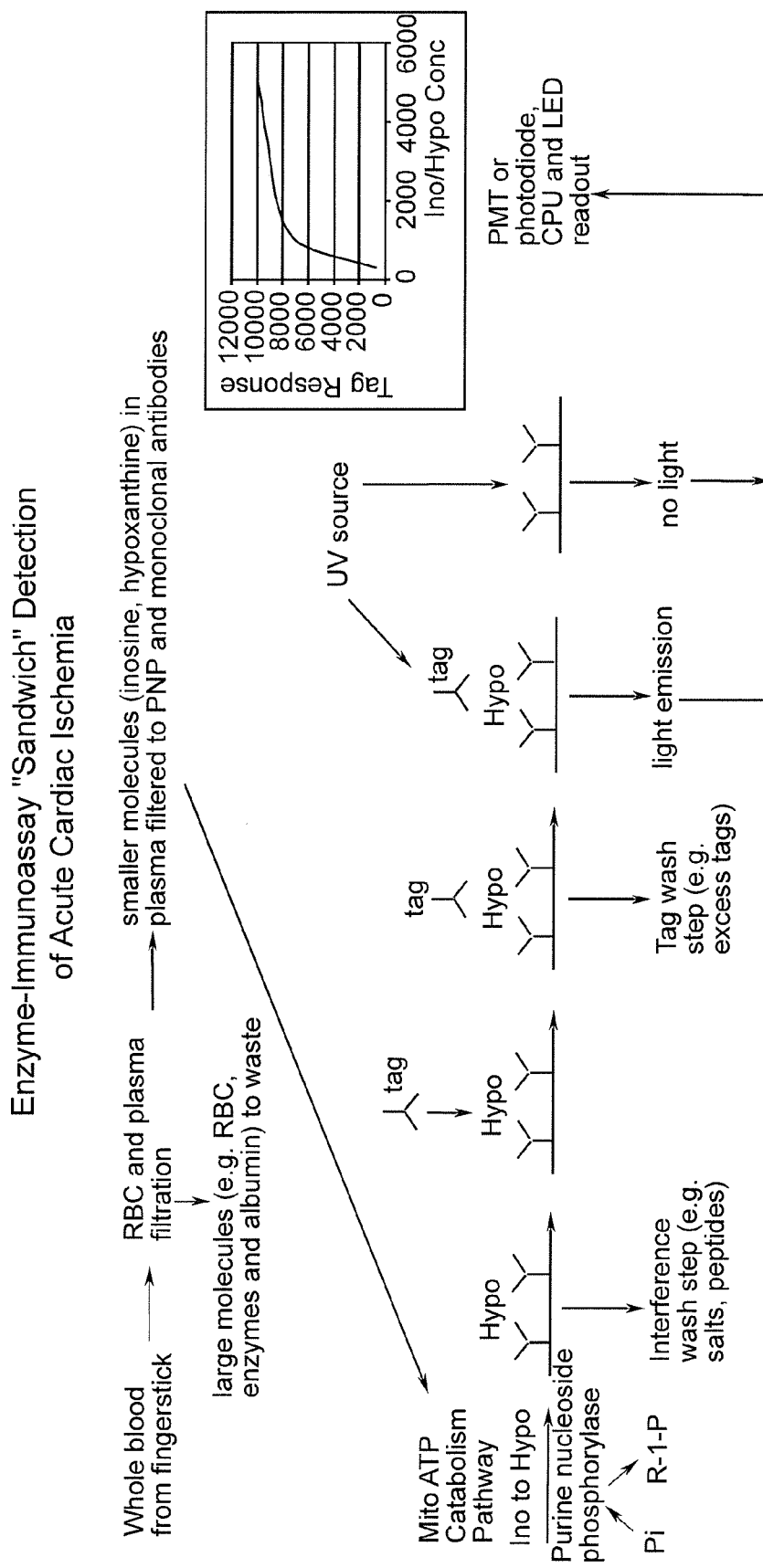
FIG. 22. Schematic of enzyme-immunoassay.

The resulting monoclonal antibody (tagged and untagged) can be utilized as shown in FIGS. 21 and 22, in a manner similar to that which is used for quantitative detection of biomarkers of acute myocardial infarction (e.g. myoglobin, CK-MB, cardiac troponin). The main advantages of using an immunoassay technique includes sensitivity (fluorescence) and specificity (antibody) in the detection of inosine and hypoxanthine, and the potential utilization of the developed antibodies in current cardiac panel assays (e.g. with myoglobin, cardiac troponin, CK-MB).

The immunoassay technique may have at least two clinical applications. The immunoassay may be added to existing hospital clinical laboratories quantitative cardiac panels. Alternatively, or in addition, the antibodies may be used on qualitative cardiac panel test strips. Both applications may be useful as a medical diagnostic tool for detection of acute cardiac ischemia in non-traumatic chest pain (or other) patients.

Point of Care (POC) Device

The invention also comprehends a rapid hand-held medical device for point-of-care whole blood levels of endogenous inosine and/or hypoxanthine, potential biomarkers of non-traumatic acute cardiac ischemia. The purpose of using the hand held medical device is to rapidly measure acute cardiac ischemia biomarkers (e.g. inosine/hypoxanthine) from a finger stick whole blood sample. The results of the evaluation should take less than 1 minute, which significantly reduces the time course for emergency medical diagnosis and treatment of individuals experiencing non-traumatic acute cardiac ischemia or impending acute myocardial infarction.

The point-of-care medical device comprises hardware (similar to that utilized in commercially available hand-held glucose meters), software (for meter operations and computations), and disposable substrate (e.g. test strips) with bound enzymes and luminescent material for direct or indirect quantification of inosine/hypoxanthine in whole blood. The handheld medical device is similar in basic operation to the commercial hand-held glucose meter used by diabetic patients. The major differences between this invention and the glucose meter are the following: the glucose meter technology utilizes glucose oxidase on the test strips and typically a potentiometric detector, whereas one embodiment of the invention utilizes enzymes PNP and XO, PHOLASIN® as the luminescent material (alternate luminescent materials can also be used), and preferably a photomultiplier tube (PMT), photodiode or an equivalent means of detection, as the detector. Luminescence technology is significantly more sensitive than the potentiometric detection. Purine nucleoside phosphorylase (PNP) and xanthine oxidase (XO), the enzymes used in the disposable test strip, are available commercially (e.g. Sigma-Aldrich, USA). The enzymes (which address enzyme substrate specificity) are covalently bound to a substrate such as a test strip, and used to convert inosine to hypoxanthine, hypoxanthine to xanthine, and xanthine to uric acid. During XO enzymatic activity, superoxide anion free radicals are generated as a by-product of enzyme turnover. PHOLASIN®, a sensitive photoprotein from a bi-valve mollusk, is also covalently bound to the test strip and generates visible light in the presence of superoxide anion free radicals to produce measurable blue-green light (luminescence, ~490 nm). Luminescence is a sensitive technique to provide an indirect measurement (measures component enzymatic conversion by-products) of inosine and hypoxanthine concentrations in whole blood. In addition, use of the medical device may be coupled to the use of cell phone technology. In this case, if measured whole blood concentrations of inosine/hypoxanthine were atypically elevated, an automatic notification could be transmitted by the medical device to activate an Emergency Medical Services system. The rapid measurement of elevated inosine and hypoxanthine in whole blood should aide EMS personnel in initiating immediate treatment for acute cardiac ischemia in non-traumatic chest pain patients.

The hand-held medical device is a rapid and quantitative instrument which may be used by hospital emergency department (ED) or EMS personnel as part of the initial medical assessment on patients presenting with non-traumatic chest pain and potential acute cardiac ischemia. Generally, the device is modular (handheld), automated and easily operated by trained individuals (e.g. emergency or other medical services personnel, or even by patients themselves). The medical device and test strips are affordable for potential use at home by individuals whose physician have classified them as at high risk for developing acute myocardial infarction (e.g. unstable angina, medical history of myocardial infarction, etc).

This aspect of the invention is illustrated schematically in FIG. 23A-B, where FIG. 23A is a flow diagram of a procedure that may be followed using the device, and FIG. 23B is a schematic representation of the device 10, which comprises substrate 11 and detector 12.

Detection Using HPLC

In some embodiments of the invention, early biomarkers of ischemia (such as inosine, xanthine, hypoxanthine, adenine and uric acid) are measured directly using chromatography methods such as HPLC. One or more, and preferably two or more, of these biomarkers may be measured in a clinical sample from a patient in order to determine whether or not the patient has or is experiencing ischemia. The sample may be exposed to PNP and/or XO enzymes as described above, or the sample may be analyzed directly with no enzymic conversion. Those of skill in the art will recognize that some preparatory steps may be taken to process the sample, e.g. centrifugation, filtration, etc. The output of the analysis is typically a direct quantification of the amount of the detected substances in the sample, based on parallel or corresponding analyses of control samples containing known quantities of the substances.

Uses of the Methods

The methods of the invention may be advantageously employed in any setting in which they would be beneficial, and especially in clinical or medical settings. In particular, any emergency facility (e.g. an emergency room, ambulance, etc.) may employ the methods. In some embodiments, the blood sample that is obtained from the patient is analyzed in a laboratory setting. However, this need not be the case. As discussed above, the methods of the invention can also be adapted for point of care use.

The assay described herein may be carried out in concert with other assays and/or tests, i.e. the assays of the invention may be part of a battery of tests which are generally used to evaluate patients with non-traumatic chest pain. However, those of skill in the art will recognize that in some circumstances persons who have experienced traumatic chest pain may also benefit from the use of the methods and devices, as well as persons who are not experiencing chest pain but may be at risk of developing cardiac ischemia. In other embodiments, the assay described herein may be combined with one or more other assays (e.g. glucose oxidase/horse radish peroxidase, HRP assay) in a single reaction, e.g. on a single test strip.

The following examples are intended to illustrate the practice of the invention but are not intended to limit the scope of the invention in any way.

EXAMPLES

Example 1

High-Performance Liquid Chromatography (HPLC) Determination of Inosine, a Potential Biomarker for Initial Cardiac Ischemia, Using Isolated Mouse Hearts Each year in the USA approximately 78 million patients with non-traumatic chest pain come to hospital emergency rooms. It is estimated that approximately 25% of these patients are experiencing cardiac ischemia, but due to the shortcomings of the available testing methods they are incorrectly diagnosed and discharged without appropriate therapy having been provided. Preliminary data with a globally ischemic mouse heart model has demonstrated that endogenous inosine might be a potential biomarker of initial cardiac ischemia before cardiac tissue necrosis. A high-performance liquid chromatographic diode array detection (HPLC-DAD) method was utilized for the detection and quantification of inosine in Krebs Henseleit (Krebs) buffer solution perfusing from surgically removed and isolated mouse hearts undergoing global cardiac ischemia. A $C_{18}$ column at a flow rate of 0.6 ml min 1 with an aqueous mobile phase of trifluoroacetic acid (0.05% trifluoroacetic acid in deionized water, pH 2.2, v/v) and methanol gradient was used for component separation. The assay detection limit for inosine in Krebs buffer solution was 500 ng ml 1 using a 100-ml neat injection. The HPLC results were used to determine total cardiac effluxed inosine into the Krebs effluent for each mouse during oxidative stress and compared with the percent cardiac ventricular functional recovery rate to determine if a relationship exists amongst this cardiovascular parameter during periods of cardiac oxidative stress.

Introduction

Cardiovascular disease (e.g. myocardial infarction) is one of the leading causes of mortality in the world (Domer & Rieder 2004, Okrainec et al. 2004, Naudziunas et al. 2005). Current medical evaluation of patients suspected of having a myocardial infarction includes an electrocardiogram blood evaluation for specific biomarkers of cardiac ischemia and where available radioisotope perfusion studies (Lees 2000, Beyerle 2002, ADAM, Inc. 2005). Blood evaluation determines the levels of several specific endogenous protein biomarkers (e.g. troponin T, troponin I, creatine kinase MB (CK-MB) and myoglobin); however, these biomarkers are normally indicative of cardiac tissue necrosis and are detected hours after the cardiac ischemic event and not at the time of initial cardiac ischemia, which may include angina (stable or unstable but non-necrotic). Ideally, emergency medical services would benefit from a biomarker of early cardiac ischemia to guide initial treatment and subsequent diagnostic steps in the chest pain patient. Medical conditions (e.g. anxiety attacks, acid reflux and angina) other than myocardial infarction that cause patient chest pain and other constitutional symptoms that might be seen as being consistent with myocardial ischemia.

To perform its circulatory function, the heart is highly energy dependent on adenosine triphosphate (ATP), which is made in cardiac cellular mitochondria by either aerobic (oxidative phosphorylation via electron transport chain) or anaerobic (glycolysis) processes. The aerobic process is heavily oxygen dependent and generates approximately 80% of cardiac cellular ATP. The anaerobic process is independent of oxygen and produces approximately 20% of the cardiac cellular ATP. Lactic acid is a by-product of anaerobic ATP production.

To produce large quantities of ATP, human cardiac cells have an abundance of mitochondria that comprise approximately 40-50% of the cardiac cellular mass. When cardiac tissue is subjected to periods of constant oxidative stress (e.g. cardiac ischemia), insufficient oxygen is available for cardiac mitochondria to synthesize aerobically the ATP required for normal cardiac function. This causes a cellular accumulation of ATP metabolic by-products (e.g. adenosine diphosphate (ADP), adenosine monophosphate (AMP)) and activates normally dormant enzymes (e.g. 5'-nucleotidase, adenosine deaminase, purine nucleoside phosphorylase and xanthine oxidase) to catabolize the ATP by-products to substances such as adenosine, inosine, hypoxanthine, xanthine and uric acid for cardiac cellular elimination (Abd-Elfattah et al. 2001). In human cardiac tissue, another source of ATP metabolic by-products is through metabolism of diadenosine polyphosphates, which are released from cardiac specific secretory granules during periods of cardiac metabolic or ischemic stress to provide cellular protective functions (Luo et al. 2004).

Inosine (9-β-D-ribofuranosylhypoxanthine) is an endogenous purine nucleoside normally found in the human body as a degradation component of purine metabolism. In human plasma, inosine is metabolized in red blood cells with a reported half-life of <5 min with endogenous plasma levels found in trace amounts (e.g. low ng ml$^{-1}$) (Viegas et al. 2000). In humans, nature has provided a cellular biochemical mechanism to help conserve energy in producing the required large quantities of ATP for cardiac cellular use (called the salvage pathway), which can convert cellular inosine back to ATP via several enzymatic steps; thus, recycling cellular inosine (Nelson & Cox 2000). However, in periods of constant cardiac oxidative stress (e.g. 20 min), cardiac cells build up significant amounts of ATP metabolic by-products, which activate normally dormant enzymes to catabolize ATP by-products, which then become systemically available before their elimination.

A recently published scientific editorial requested the need for an initial biomarker for cardiac ischemia before cardiac tissue necrosis (cardiac proteins found in plasma after several hours of cardiac ischemia) (Morrow et al. 2003). This initial biomarker would aid Emergency Medical Services (EMS) personnel in the rapid treatment of initial cardiac ischemia (potentially myocardial infarction), thus potentially increasing the survival rate of myocardial infarction victims every year. One recent publication (Bhagavan et al. 2003) addressing the scientific editorial request describes a blood measurement for serum albumin that appears at an elevated level in the blood in patients undergoing myocardial infarction. However, the authors state that the colorimetric method would not discriminate between ischemic patients with and without myocardial infarction, thus the need for a method to detect the initial cardiac ischemic event before myocardial infarction would be beneficial to EMS personnel.

Before extracellular biomarkers (e.g. serum albumin) appearing in the blood from cardiac ischemic events, plasma inosine levels would be elevated significantly above the normally low endogenous levels thus becoming a useful biomarker of pre-necrosis cardiac ischemia. Adenosine, another nucleoside metabolic by-product of ATP catabolism, is metabolized by red blood cells and has a very short plasma half-life (e.g. approximately 15 seconds); thus making it more difficult to measure it quantitatively in plasma (Mei et al. 1996).

The Institute of Cancer Research (ICR) outbred mouse (Dohm 2004) was used as the animal model for all global cardiac ischemia experiments using a Langendorff apparatus (Xi et al. 1998). For sample analysis, a high-performance liquid chromatographic diode array detection (HPLC-DAD) method was utilized consisting of direct injection of the Krebs buffer eluant from surgically removed and perfused mouse heart tissue. In addition, the HPLC-DAD method utilized current column technology (hydrophobic/hydrophilic reverse-phased retention), which provided sufficient component resolution and sensitivity for adenosine, inosine and xanthine-like derivatives. The HPLC-DAD results were used to compute the inosine area under the concentration (AUC) time curve from mouse Krebs buffer eluant samples and compared with the percent cardiac ventricular functional recovery rate to determine if a relationship exist between this cardiovascular parameter during periods of constant cardiac oxidative stress.

Materials and Methods

Chemicals, Mobile Phase and Krebs Buffer Solution

Hypoxanthine and xanthine were purchased from Acros Organics (Fair Lawn, N.J., USA). 2,3-Dihydroxybenzoic acid (DHBA), 2,5-dihydroxybenzoic acid, salicylic acid (SA), adenosine, inosine and uric acid were purchased from Sigma-Aldrich (St Louis, Mo., USA). Sodium chloride, sodium bicarbonate, potassium chloride, magnesium sulfate, monobasic potassium dihydrogen phosphate, dextrose and calcium chloride were used to prepare the Krebs buffer solution, and all were purchased from Sigma-Aldrich. All purchased chemicals were ACS reagent grade or better. The Krebs buffer solution (118.5 mM NaCl, 25.0 mM NaHCO$_3$, 11.1 mM C$_6$H$_6$O$_6$, 4.7 mM KCl, 1.2 mM KH$_2$PO$_4$, 1.2 mM MgSO$_4$ and 2.5 mM CaCl$_2$) was prepared in ultrapure deionized water at pH 7.4 and with a 95% O$_2$:5% CO$_2$ ratio. For mobile phase preparation, trifluoroacetic acid (TFA) was reagent grade and methanol was Optima HPLC-grade; both were purchased from Fisher Scientific (Fair Lawn, N.J., USA). Ultrapure distilled and deionized water (18 megaohm) used for HPLC work was prepared in-house using the Purelab Ultra deionized water system (US Filter, Lowell, Mass., USA) and filtered before use.

Preparation of Standard Solutions

Stock standards of adenosine, inosine, hypoxanthine, xanthine and uric acid (100 μg ml$^{-1}$) were prepared in deionized water and stored at 4° C. Working standards of each component were prepared at 2.5 μg in Krebs buffer solution and maintained at −20° C. along with the mouse Krebs buffer eluant samples. The working standards stored at −20° C. were stable for at least 6 months.

HPLC-DAD, High-Performance Liquid Chromatography-Mass Spectrometry (HPLC-MS) Equipment and Conditions For inosine quantification and diode array spectral purity, the HPLC equipment consisted of an Agilent Model 1100 Quaternary HPLC-DAD and Chemstation software (Palo Alto, Calif., USA). The DAD was set to acquire a complete ultraviolet light spectrum for component specificity with 240 nm used for quantification of inosine and the other ATP metabolic by-products. For inosine confirmation, liquid chromatography/mass spectrometry (LC/MS) was used and the equipment consisted of a Shimadzu LCMS-2010A HPLC coupled to a single quadrapole mass spectrometer using LCMS Solutions software (Columbia, Md., USA). The HPLC-MS conditions consisted of using electrospray ionization (ESI) with the following instrument set points (heating block at 300° C., nebulizer at 4 liters/per minute nitrogen, interface voltage at 2 kV) and full-scan acquisition using a positive-ion mode.

The analytical column for both HPLC-DAD and HPLC-MS analysis was a Synergi™ Hydro-RP $C_{18}$, 150×3 mm i.d., 4 mm packing, 80 Å (Phenomenex, Torrance, Calif., USA). The $C_{18}$ guard column was a 30×4.6 mm i.d., 40-50 μm pellicular packing (Alltech, Deerfield, Ill., USA). The mobile phase consisted of aqueous trifluoroacetic acid (0.05% TFA in deionized water, v/v, and pH 2.2) and methanol gradient. The mobile phase gradient was linear with a time-course as follows (95:5 0.05% TFA in deionized water:methanol, v/v at 0 min; 70:30 0.05% TFA in deionized water:methanol, v/v at 12 min; 10:90 0.05% TFA in deionized water:methanol, v/v at 13 min and held 3 min, and 95:5 0.05% TFA in deionized water:methanol, v/v at 17 min).

The mobile phase was degassed automatically using an Agilent 1100 membrane degasser with a flow-rate of 0.6 ml min 1. An injection volume of 100 ml of the Krebs buffer eluant was made using an autosampler. The typical HPLC operating pressure was approximately 150 bar with ambient column oven temperature and 345 kPa backpressure regulator (SSI, State College, Pa., USA) to prevent mobile phase outgassing in the detector.

ICR Mouse Experiment Conditions

ICR mice were used for all cardiac ischemia experiments with morphometric characteristics and baseline cardiac function of the adult mice (ICR strain) provided in Table 1. The mice were anaesthetized; hearts were surgically removed and isolated using the Langendorff apparatus. Global cardiac oxidative stress was accomplished by adjusting the Krebs-buffered solution to zero flow through the heart for 20 min. Upon heart reperfusion, approximately 1.5-ml samples of Krebs-buffered eluant from the isolated mouse hearts were collected at predetermined time-points (0, 1, 3, 5, 10 and 20 min) in plastic bullet centrifuge tubes and frozen at −20° C. until HPLC-DAD analysis.

To evaluate the effects of oxidative stress on the mouse heart, established cardiovascular measurements (e.g. ventricular functional recovery) were performed on both control and test animals. The methodology used to evaluate the isolated perfused mouse heart has been previously described (Xi et al. 1998). In brief, animals were anaesthetized with an intraperitoneal injection of pentobarbital sodium (100 mg kg$^{-1}$, with 33 IU heparin added). The heart was removed and immediately placed in ice-cold Krebs buffer. The aorta was cannulated within 3 min onto the Langendorff perfusion system and the heart was perfused in a retrograde fashion at a constant pressure of 55 mm Hg with Krebs buffer gassed with 95% $O_2$ and 5% $CO_2$. The pH of the buffer and the heart temperature were maintained at 7.35-7.50 and 37±0.5° C., respectively. A force-displacement transducer (Grass, FT03) was attached to the apex via a metal hook/surgical thread/pulley system to record and measure the ventricular contractile force and heart rate continuously. For each heart the resting tension was set at approximately 0.3 g in the beginning of the experiment.

The protocol for the test group consisted of 30 min of stabilization, 20 min of zeroflow global ischemia, and 30 min of reperfusion (Xi et al. 1998). Time-matched normoxic perfusion was carried out for the control group. At the end of each experiment, the heart was removed from the Langendorff system, quickly weighed and stored at −20° C.

Sample Preparation, Stability and Instrument Precision Evaluation

Before HPLC analysis, perfusate samples frozen at −20° C. were thawed to ambient temperature, mixed thoroughly by inversion and transferred to plastic autosampler vials for subsequent direct injection into the HPLC-DAD system. To evaluate sample stability in the perfusate solution and instrument precision; prepared samples in autosampler vials were stored at ambient laboratory temperature overnight and reinjected (n=3 times) into the HPLC for analysis.

TABLE 1

Morphometric characteristics and baseline cardiac function of the adult mice (ICR strain).

|  | Control (n/6) | Ischemia reperfusion test (n/6) |
|---|---|---|
| Body weight (g) | 42.2 ± 1.3 | 38.7 ± 2.1 |
| Heart wet weight (mg) | 258 ± 6 | 242 ± 14 |
| Heart rate (beats per minute, bpm) | 368 ± 23 | 345 ± 23 |
| Developed force (g) | 0.81 ± 0.19 | 1.12 ± 0.12 |
| Rate force product (g/bpm) | 308 ± 80 | 372 ± 49 |
| Coronary flow (ml min 1) | 2.3 ± 0.2 | 1.7 ± 0.1 |

Values are the mean ± standard error of the mean (SEM). No significant difference (p > 0.05) between the groups was found for the listed parameters, except coronary flow.

Component Retention Times, Inosine Calibration and AUC Calculations

During HPLC method development and validation, combined standards of adenosine, inosine, hypoxanthine, xanthine and uric acid were prepared in Krebs buffer solution at concentration levels of 1, 2.5, 5, 10 and 25 μg ml$^{-1}$. Standard curve linearity (non-weighted) of all components was acceptable with all correlation coefficients >0.995. During subsequent analytical runs, a single point calibration standard mixture containing 2.5 μg ml$^{-1}$ of each component was prepared in Krebs buffer solution and was used to identify component retention times and the quantification of inosine found in test samples. Using ultraviolet light detection at 240 nm, component peak area and external standardization were used for inosine computations. To determine inosine AUC on the test samples, the trapezoidal rule computation using Excel® software (a spread sheet available from Microsoft Corporation) was performed on inosine sample values from 0 to 20 min.

Results and Discussion

Initial Evaluation for (˙OH) Free Radicals

During periods of cardiac oxidative stress (e.g. acute myocardial infarction), the heart is deprived of the oxygen needed for ATP synthesis. In the absence of oxygen, dormant enzymes activate whereby ATP is sequentially converted to ADP, AMP, adenosine, inosine and hypoxanthine. Upon reperfusion of the heart with oxygenated blood or oxygenated Krebs solution, additional cellular enzymatic conversions transpire with the xanthine oxidase converting hypoxanthine to xanthine and uric acid. A metabolic by-product of xanthine oxidase is the formation of hydrogen peroxide ($H_2O_2$), which is normally converted by glutathione peroxidase to $H_2O$. However, in the presence of $Fe_2$, $H_2O_2$ may be converted to a hydroxyl free radical (˙OH) via the Fenton and Haber Weiss reactions (FIG. 1) (IUPAC 1997).

The (˙OH) is a known potent reactive oxygen species (ROS) and can cause damage to cellular components (e.g. lipids, proteins, nucleic acids) (Tardif & Bourassa 2000). To investigate the formation of ROS, one research objective was to evaluate and estimate the amount of (˙OH) generated from 20 min of global cardiac ischemia using isolated mouse hearts. In several of the initial experiments, SA (1 mM) was fortified in the Krebs buffer solution (pH adjusted 7.4) to react with (OH) and form the reaction products of 2,3- and 2,5-DHBA isomers (Onodera & Ashraf 1991, Coudray & Favier 2000). The HPLC-DAD conditions that were used for inosine determination resolved prepared standards (13 ng ml 1 or 86 nM) of the 2,3- and 2,5-DHBA isomers from other Krebs eluant sample components (e.g. SA, adenosine, inosine, hypoxanthine, etc.).

However, in the experiments performed using SA we did not observe either the 2,3- or 2,5-DHBA isomers in the sample chromatograms from mouse hearts subjected to global cardiac ischemia. It is possible that the initial level of SA (1 mM) added to the Krebs buffer solution increased the total solute concentration to a level, which reduced the solubility of 2,3- and 2,5-DHBA isomers and therefore made each analytically undetectable. Lower concentrations of SA (e.g. ≤1 μM) may in theory resolve this aspect of ROS generation from mouse global cardiac ischemia.

HPLC-DAD and HPLC-MS Confirmation

The HPLC-DAD method was used for determining all of the following components (adenosine, inosine, hypoxanthine, xanthine, uric acid, 2,3- and 2,5-DHBA isomers). The mobile phase aqueous component 0.05% TFA in deionized water was chosen as a pH of approximately 2.3 provided good peak shapes on all components and a low pH was necessary to reduce peak tailing on the acidic components (e.g. 2,5-DHBA has a pKa ~2.9). The Synergi™ Hydro-RP $C_{18}$ (polar end-capped) and Synergi™ Polar-RP $C_{18}$ (ether-linked phenyl) columns of identical dimensions were evaluated for use. While both columns worked well for inosine and polar components (e.g. adenosine), the Synergi™ Hydro-RP $C_{18}$ was selected for overall analysis as it provided good component peak shape and sufficient resolution of all components.

Figure 2:
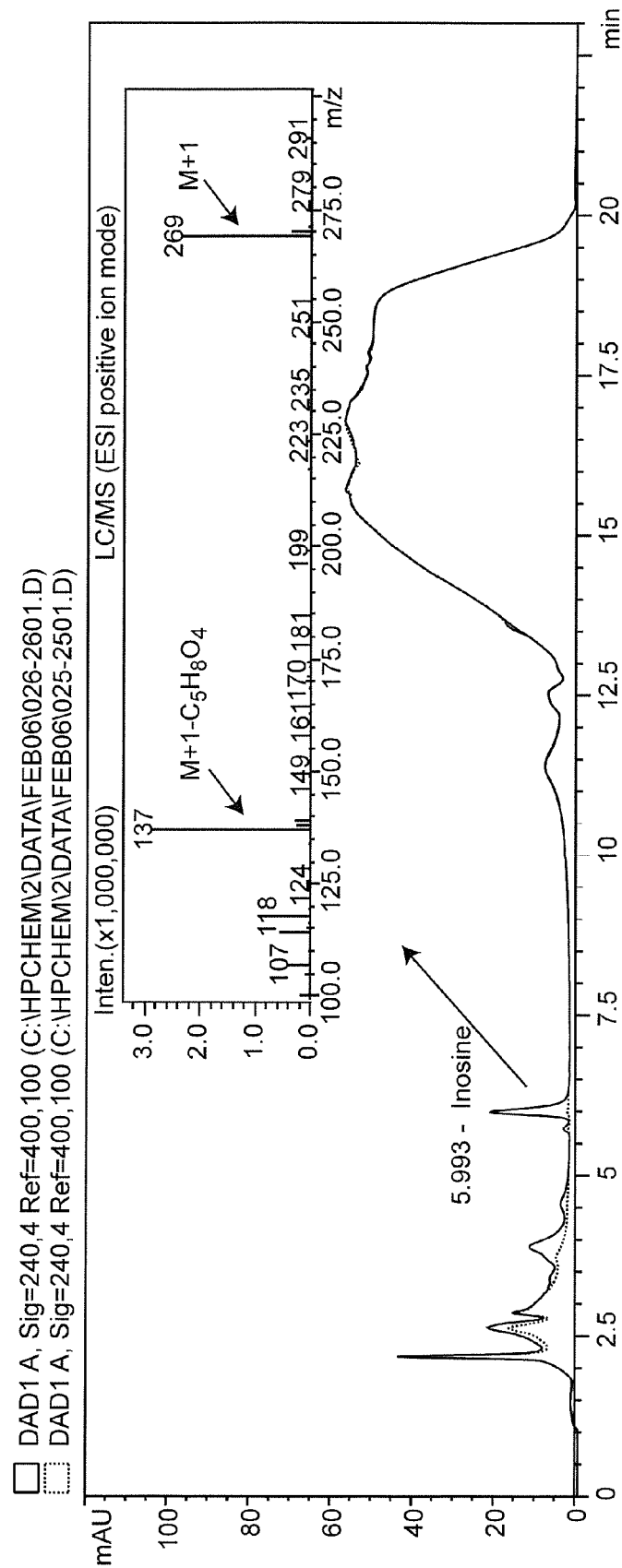
FIG. 2. A, High-performance liquid chromatographic diode array detection (HPLC-DAD) chromatograms overlay of control (025-2501.D) and 20-min global cardiac ischemia (026-2601.D) mouse perfusate samples. Inosine (retention time/5.9 min) and high-performance liquid chromatography-electrospray ionization-mass spectrometry (HPLC-ESI/MS) identifying inosine (MW/268 Da) as an early biomarker of global cardiac ischemia is demonstrated in the ischemic mouse heart perfusate.

Other components evaluated using this method have HPLC retention times as follows: uric acid, 2.8 min; hypoxanthine, 3.9 min; xanthine, 4.2 min; adenosine, 5.7 min; CK-MB, 8.2 min; 2,3-DHBA, 8.4 min; 2,5-DHBA, 10.2 min; myoglobin, 14.1 min; atrial natriuretic peptide, 14.5 min; brain natriuretic peptide, 15.0 min; and salicylic acid, 15.4 min. Both troponin I and troponin T were not detected using this HPLC method. An HPLC-DAD chromatogram overlay from a mouse subjected to 20-min global cardiac ischemia and a control mouse (non-ischemia) are presented in FIG. 2 with inosine elution at 5.9 min.

To evaluate perfusate sample stability, the prepared samples were initially injected and analysed by HPLC-DAD. The samples were subsequently stored overnight on the autosampler at ambient laboratory temperature and re-injected (n=3 times) to evaluate both for changes in component levels due to possible synthesis or degradation reactions from potential enzymes eluted in the perfusate and to evaluate instrument precision. In all re-injected perfusate samples, component levels remained constant (5/4% RSD) indicating stability overnight at ambient temperature and the absence of appreciable levels of nucleoside and purine converting enzymes in the perfusate.

HPLC-MS Confirmation of Inosine as Potential Initial Ischemia Biomarker

An HPLC-MS was used to confirm inosine at retention time 5.9 min in samples from test mice subjected to oxidative stress. The HPLC analytical column, mobile phase gradient and flow rate were identical to that used in the HPLC-DAD method. The mass spectrum for inosine (MW=268 Da) is presented in FIG. 2. It was acquired using the MS positive-ion mode, which provided a good mass spectral quality match against a prepared standard of inosine in Krebs buffer solution. The full-scan spectrum was achieved using up-front collision-induced dissociation (CID) and nitrogen as the collision gas. The mass spectrum base peak (137 Da) represents the cleavage of the ribose entity from inosine leaving a protonated hypoxanthine (MW=136 Da).

Evaluation of Inosine AUC and Other Cardiovascular Parameters

Figure 3:
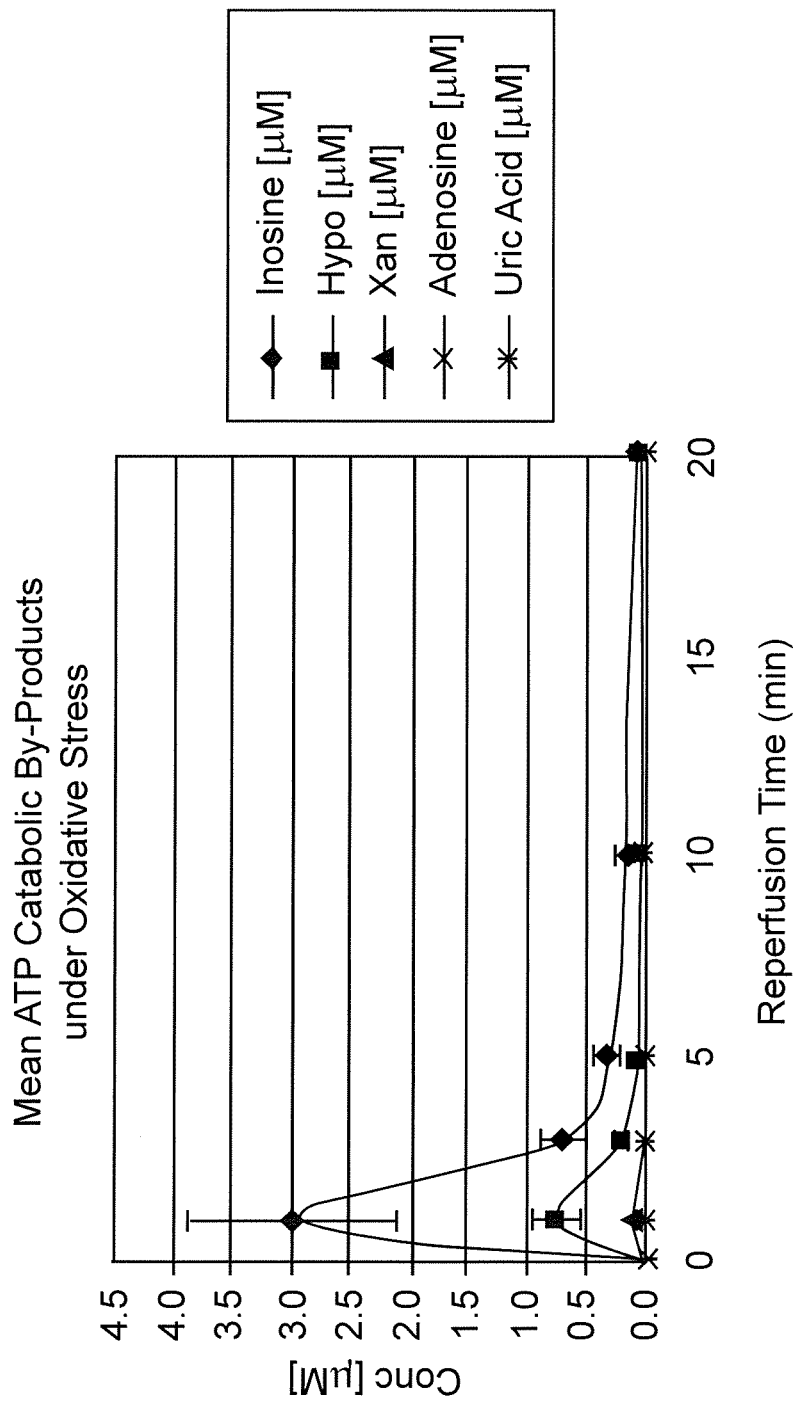
FIG. 3. Profile of adenosine triphosphate (ATP) catabolism by-products found in Krebs solution versus reperfusion time after 20-min mouse global cardiac ischemia. Inosine (µg ml$^{-1}$) levels were 0, 7.5, 2.1, 1.1, 0.4 and not detected for sample time points 0, 1, 3, 5, and 20 min, respectively.
Figure 4A:
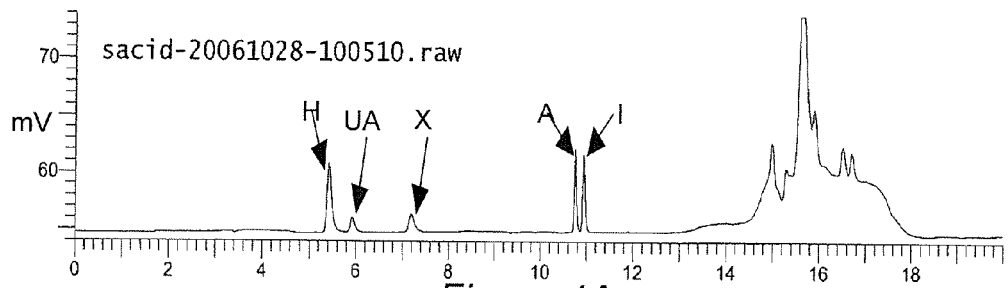
FIG. 4A-E. Chromatograms illustrating (A) 2000 ng/mL hypoxanthine (RT ~5.3 min), uric acid (RT ~5.8 min), xanthine (RT ~7.2 min), adenosine (RT ~10.7 min) and inosine (RT ~10.9 min) in deionized water, (B) low standard of 250 ng/mL hypoxanthine and inosine in blank plasma, (C) blank plasma, (D) plasma sample from healthy female subject and (E) plasma sample from hospital emergency room female patient.
Figure 4B:
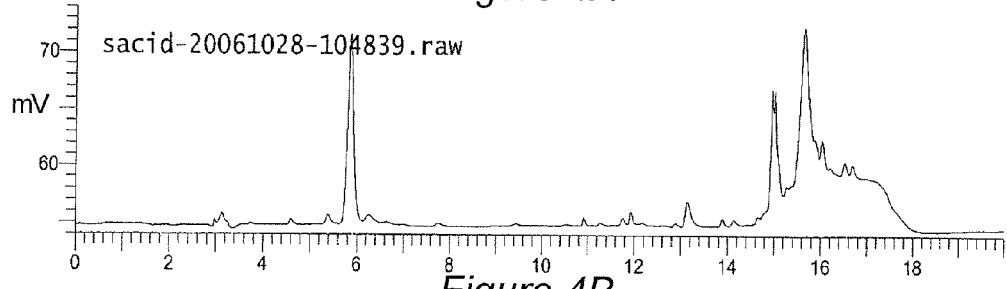
Figure 4C:
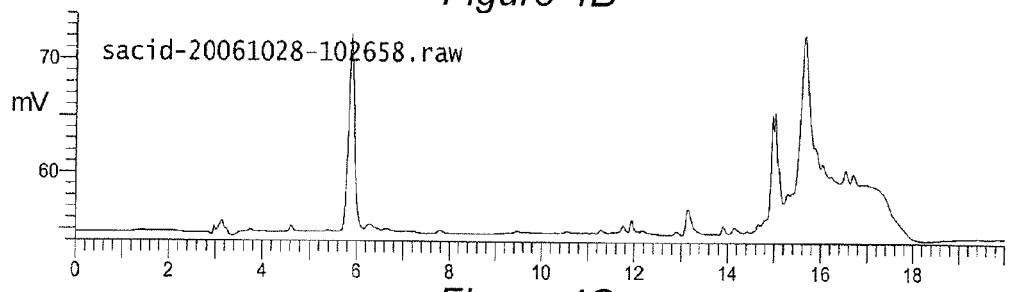
Figure 4D:
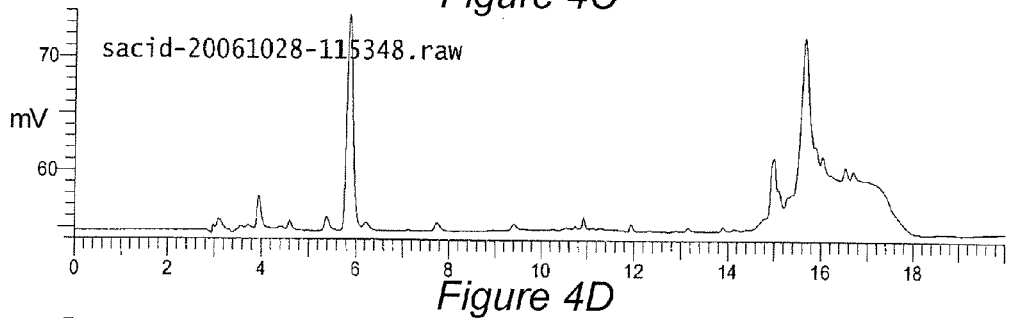
Figure 4E:
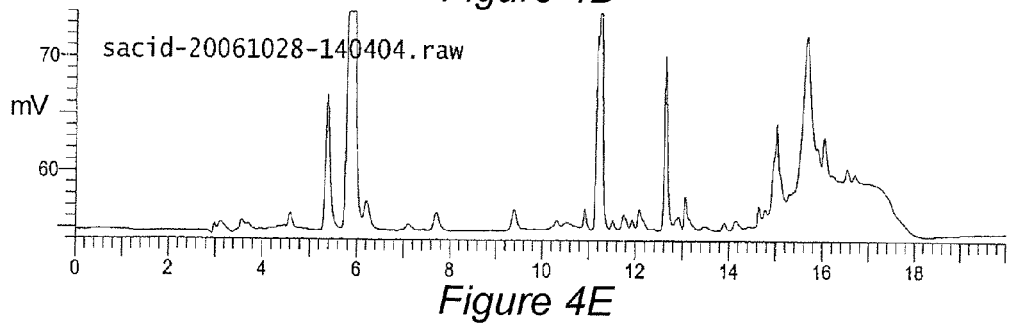

Initially, the focus was on identifying cardiac protein or peptide biomarkers (e.g. Atrial Natriuretic Peptide, Brain Natriuretic Peptide, that may be released from ischemic myocardium; however, in comparison with non-ischemic mouse hearts only inosine (22-69-fold) and xanthine-like products (e.g. hypoxanthine (>7x), xanthine (approximately 3x), uric acid (approximately 3x) were found at higher levels in globally ischemic mouse hearts. FIG. 3 is a representative profile of one mouse heart subjected to oxidative stress with the individual ATP degradation by-product components DAD response plotted against Krebs buffer reperfusion time. As can be seen, inosine was the component that had the highest DAD response with detectable component amounts found at lower mg ml 1 levels (e.g. in a range of 0.4-7.5 μg ml$^{-1}$ in mouse #874) in the sample less than 5 min following reperfusion.

Other cardiovascular parameters (e.g. the percent cardiac ventricular functional recovery rate) were measured and reported with the calculated inosine AUC results (Table 2). As can be seen in Table 2, inosine efflux was present in test mouse heart perfusate samples that were subjected to oxidative stress and was not detected in control mouse heart perfusate samples. However, for both controls and test mice, the percent cardiac functional recovery rate ranged from 39 to 92%, with the lowest measured cardiac functional recovery being in test mouse hearts that had the largest amount of inosine present in the Krebs buffer solution (e.g. test mouse with 2469 ng min ml$^{-1}$ AUC inosine effluxed with a 39% cardiac functional recovery rate). This may indicate that mouse hearts are injured to a greater degree from the effects of oxidative stress efflux more inosine from ATP by-product degradation.

TABLE 2

Inosine washout and cardiac ventricular functional recovery in Langendorff mouse hearts following aerobic perfusion and 20-min global ischemia.

| Sample type | Inosine area under the curve (AUC) 0-20 min (ng min ml$^{-1}$) | Cardiac Functional recovery rate (%) |
| --- | --- | --- |
| Control | n.d.* | 70 |
| Control | n.d. | 72 |
| Control | n.d. | 74 |
| Control | n.d. | 82 |
| Control | n.d. | 81 |
| Control | n.d. | 64 |
| Test | 653 | 92 |
| Test | 962 | 84 |
| Test | 954 | 77 |
| Test | 1003 | 53 |
| Test | 2469 | 39 |
| Test | 2583 | 52 |

*n.d., Not detected.

Conclusions

These results suggest that the level of inosine found in test animals subjected to cardiac oxidative stress may serve as a biomarker indicative of early cardiac ischemia. This can be explained by ischemic myocytes undergoing nucleotide purine catabolism in the absence of oxygen with subsequent activation of dormant cellular enzymes and the generation of degradative breakdown products of ATP.

References for Example 1

ADAM, Inc. 2005. Heart attack and acute coronary syndrome (available at the website located at adam.about.com/reports/

Abd-Elfattah A S, Higgins R S D, Latifi R, Merrell R C. 2001. Targeting post-ischemic repurfusion injury: scientific dream and clinical reality. New Surgery 1:41 51.

Beyerle K. 2002. POC testing of cardiac markers enhances ED care. Nursing Management 33(9):37 39.

Bhagavan N V, Lai E M, Rios P A, Yang J, Ortega-Lopez A M, Shinoda H, Honda S A A, Rios C N, Sugiyama C E, Ha C. 2003. Evaluation of human serum albumin cobalt binding assay for the assessment of myocardial ischemia and myocardial infarction. Clinical Chemistry 49(4):581 585.

Coudray C, Favier A. 2000. Determination of salicylate hydroxylation products as an in-vivo oxidative stress marker. Free Radical Biology and Medicine 29(11):1064 1070.

Dohm M. 2004. Origin and maintenance of the Hsd:ICR random-bred strain (available at website located at www2.hawaii.edu/approximately dohm/Phd/OriginHsd.htm)

Dorner T, Rieder A. 2004. Risk management of coronary heart disease-prevention. Wiener Medizinische Wochenschrift 154(11 12):257 265.

IUPAC. 1997, Fenton and Haber Weiss reactions. IUPAC Compendium of Chemical Terminology 69: 1274 1277.

Lees K. 2000. Multiple marker test quickly identifies high-risk heart attack patients, study says. Heart Signs, Duke University News and Communications available at website located at dukenews.duke.edu Luo J, Jankowski V, Gungar N, Neumann J, Schmitz W, Zidek W, Schluter H, Jankowski J. 2004. Endogenous diadensoine tetraphosphate, diadensoine pentaphosphate, and diadenosine hexaphosphate in human myocardial tissue. Hypertension 43(5):1055 1059.

Mei D A, Gross G J, Nithipatikom K. 1996. Simultaneous determination of adenosine, inosine, hypoxanthine, xanthine, and uric acid in microdialysis samples using microbore column high-performance liquid chromatography with a diode array detector. Analytical Biochemistry 238:34 39.

Morrow D A, De Lemos J A, Sabatine M S, Antman E M. 2003. The search for a biomarker of cardiac ischemia. Clinical Chemistry 49(4):537 539.

Naudziunas A, Jankauskiene L, Kalinauskiene E, Pilvinis V. 2005. Implementation of the patient education about cardiovascular risk factors into a daily routine of the Cardiology Unit of the hospital. Preventive Medicine 41(2):570 574.

Nelson D, Cox M. 2000. Lehninger principles of biochemistry. 3rd ed. New York, N.Y.: Worth. p. 848 868.

Okrainec K, Banerjee D K, Eisenburg M J. 2004. Coronary artery disease in the developing world. American Heart Journal 148(1):7 15.

Onodera T, Ashraf M. 1991. Detection of hydroxyl radicals in the post-ischemic reperfused heart using salicylate as a trapping agent. Journal Molecular Cellular Cardiology 23:365 370. Tardif J, Bourassa M. 2000. Antioxidants and cardiovascular disease. Dordrecht: Kluwer. p. 57 70.

Viegas T X, Omura G A, Stoltz R R, Kisick J. 2000. Pharmacokinetics and pharmacodynamics of peldesine (BCX-34), a purine nucleoside phosphorylase inhibitor, following single and multiple oral doses in healthy volunteers. Journal Clinical Pharmacology 40:410 420. Xi L, Hess M L, Kukreja R C. 1998. Ischemic preconditioning in isolated perfused mouse heart: Reduction in infarct size without improvement of post-ischemic ventricular function. Molecular and Cellular Biochemistry 186:69 77.

Example 2

An HPLC Method for Determination of Inosine and Hypoxanthine in Human Plasma from Healthy Volunteers and Patients Presenting with Potential Acute Cardiac Ischemia Abstract A simple and sensitive high-performance liquid chromatography (HPLC) method utilizing ultraviolet (UV) detection was developed for the determination of inosine and hypoxanthine in human plasma. For component separation, a monolithic C18 column at a flow rate of 1.0 mL/min with an aqueous mobile phase of trifluoroacetic acid (0.1% TFA in deionized water pH 2.2, v/v) and methanol gradient was used. The method employed a one-step sample preparation utilizing centrifugal filtration with high component recoveries (~98%) from plasma, which eliminated the need of an internal standard. The method demonstrated excellent linearity (0.25-5 g/mL, R>0.9990) for both inosine and hypoxanthine with detection limits of 100 ng/mL. This simple and cost effective method was utilized to evaluate potential endogenous plasma biomarker(s), which may aid hospital emergency personnel in the early detection of acute cardiac ischemia in patients presenting with non-traumatic chest pain.

Introduction

According to a recent report by the World Health Organization (WHO, 2002 data), approximately 32 million myocardial infarctions (MI) occurred worldwide resulting in more than 12 million deaths [1]. Cardiovascular disease is the leading cause of mortality in the world and includes MI, which can be presaged by acute cardiac ischemia [2-5]. In a patient suspected of having an MI or on-going acute cardiac ischemia, standard diagnostic procedures include patient history and physical exam, an electrocardiogram (ECG) and sequential assessment of biomarkers of myocardial damage [6-8].

Current test methods for endogenous cardiac biomarkers (e.g. cardiac troponin I, creatine kinase-MB and myoglobin) include LC-MS analysis [9,10] and fluorescence immunoassay [11-14]; however elevation of these protein biomarkers reflect some level of myocardial necrosis, and are typically elevated in a diagnostic range several hours after acute myocardial infarction. Inosine (9-β-d-ribofuranosylhypoxanthine, MW 268 Da nucleoside) and hypoxanthine (1,7-dihydro-6H-purin-6-one, MW 136 Da purine) are endogenous non-protein plasma constituents normally found at low concentrations (e.g. ~200-400 ng/mL) in human plasma resulting from dietary and endogenous purine metabolism [15]. As described in Example 1, inosine levels increase from cardiac tissue subjected to constant conditions of oxidative stress (e.g. acute cardiac ischemia or myocardial infarction).

Current methods for plasma level measurement of selected ATP catabolic by-products such as inosine, hypoxanthine, xanthine and uric acid, in plasma utilize HPLC-UV with sample preparation steps including solid phase extraction [15], protein precipitations (e.g. ethanol or TCA) as well as some methods requiring use of an internal standard [17,18]. High performance liquid chromatography (HPLC) with ion pairing reagents [19-21] or protein precipitation and enzyme catalyzed luminescence detection [22] have also been used. One HPLC method utilized centrifugal filtration for sample preparation; however this method did not completely resolve hypoxanthine and xanthine components and column degradation was reported after 3 months of use [23]. None of these techniques, however, offers as simple a determination for inosine and hypoxanthine (can also evaluate uric acid, adenosine and xanthine) in human plasma as the method described herein. The method utilizes centrifugal membrane filter technology and does not require the use of an internal standard. In addition, this method employs a recently introduced HPLC column technology (Onyx™ monolithic column, Phenomenex® Inc. 2005 market introduction) [24], which provides sufficient component resolution and sensitivity for measurement of inosine and hypoxanthine in human plasma samples, from healthy volunteers and emergency room patients presenting with chest pain with and without acute cardiac ischemia.

Experimental

Chemicals and Blank Plasma

Hypoxanthine and xanthine were purchased from Acros Organics (Fair Lawn, N.J., USA) and adenosine, inosine and uric acid were purchased from Sigma-Aldrich (St. Louis, Mo., USA) with all chemicals being ACS reagent grade or higher purity. For mobile phase preparation, trifluoroacetic acid (TFA) was reagent grade, methanol was Optima HPLC grade and both were purchased from Fisher Scientific (Fair Lawn, N.J., USA). Ultrapure distilled and deionized water (18M cm) used for all HPLC work was prepared in-house using PureLab® Ultra water purification system (US Filter, Lowell, Mass., USA) and 0.2 m filtered prior to use. Blood bank human blank plasma used for preparation of controls was provided by VCU Medical Center, Richmond, Va., USA.

HPLC Equipment and Mobile Phase

The HPLC-DAD (diode array detector) equipment consisted of a Hewlett-Packard (HP) Model 1090 HPLC system (Agilent Technologies, Palo Alto, Calif., USA). The analytical column used was a Phenomenex® Onyx™ monolithic $C_{38}$, 20 cm×4.6 mm I.D., 130 Å column coupled to an Onyx™ $C_{18}$ guard column, 5 cm×4.6 mm I.D. (Torrance Calif., USA). The guard column was replaced after each analytical run of approximately 50 samples. The mobile phase consisted of aqueous trifluoroacetic acid (0.1% TFA in deionized water, pH 2.2, v/v) and methanol gradient. The mobile phase gradient was programmed with time course as follows (99:1 0.1% TFA in deionized water:methanol (v/v) at 0 min and held for 3 min; 70:20 0.1% TFA in deionized water:methanol (v/v) at 10 min; 5:90 0.1% TFA in deionized water:methanol (v/v) at 11 min and held 2 min, and 99:1 0.1% TFA in deionized water:methanol (v/v) at 14 min). The mobile phase was continuously degassed using helium sparging and used at a flow rate of 1.0 mL/min. Typical HPLC operating pressure at gradient time 0 min conditions was approximately 84 bar with ambient column temperature. An injection volume of 15 L of the prepared plasma sample was accomplished using the HP Model 1090 autosampler. Component detection was achieved using the HP Model 1090 DAD detector with data collection at the optimal UV wavelength absorption of 250 nm for both inosine and hypoxanthine. The detector was operated at high sensitivity set point with a 1 s response time. A 345 kPa backpressure regulator (SSI, State College, Pa., USA) was coupled to the detector outlet to prevent mobile phase outgassing. Data acquisition and component computations were performed using Total-Chrom™ Workstation software (Perkin Elmer™, Norwalk, Conn., USA).

Standard and Control Preparation

Stock standards of adenosine, inosine, hypoxanthine, xanthine and uric acid (100 g/mL) were prepared in deionized water and stored at 4° C. Working standards to establish HPLC retention times of adenosine, xanthine and uric acid components were prepared at 2.5 µg/mL concentrations in deionized water. Working standards of inosine and hypoxanthine (250, 500, 1000, 3000 and 5000 ng/mL) were prepared in deionized water. All working standards were stored at −70° C. and stable for at least 6 months. Working controls of inosine and hypoxanthine (250, 2000 and 4000 ng/mL) were prepared using pooled hospital blood plasma (n=3 donated lots) which were evaluated individually and confirmed to lack detectable levels of inosine and hypoxanthine components.

It is possible the levels of inosine and hypoxanthine in blood bank plasma were not detectable due to the time (>10 days) the plasma was stored refrigerated (4° C.) prior to expiration and availability for laboratory experimental use. Without freezing the plasma or utilizing plasma enzyme inhibitors, xanthine oxidase and purine nucleoside phosphorylase found in plasma may metabolize the normally low levels of inosine and hypoxanthine to their end product uric acid. Following preparation of control samples, they were immediately frozen at −70° C., to prevent endogenous plasma purine nucleoside phosphorylase from converting inosine to hypoxanthine prior to formal sample analysis. Following hospital approval, blood was obtained from hospital emergency room patients (n=20), in vacutainer TM tubes containing heparin as per hospital emergency room protocols for patients presenting with chest pain and potential MI or acute myocardial ischemia. Sample tubes were centrifuged at ~1000×g for 10 min with plasma drawn off and split into tubes for hospital clinical testing and one tube immediately frozen at −20° C. (transferred to −70° C. for storage) for inosine and hypoxanthine analysis. Plasma samples from healthy blood donors (male and female, both genders>18 years of age) were purchased from ProMedDx (Norton, Mass., USA) which used an IRB approved specimen collection protocol and stored frozen at −70° C. Prior to HPLC analysis, plasma samples were thawed to ambient temperature, mixed thoroughly by inversion and centrifuged at 1000×g for 10 min to eliminate fibrinous material.

Sample Preparation

Samples were prepared for HPLC analysis by pipetting 250 μl of plasma into a polypropylene Microcon® YM-10 (10,000 molecular weight cutoff, MWCO) centrifugal filter tube (Millipore, Bedford Mass., USA). The sample tubes were capped and centrifuged at 14,000×g for 15 min at ambient lab temperature. The clear filtrates were transferred to deactivated glass HPLC autosampler vials (Waters®, Milford Mass., USA) with 15 μL injected into the HPLC system for analysis.

Results and Discussion

HPLC Conditions Optimization

Several types of $C_{18}$ columns were evaluated for resolving adenosine, inosine, hypoxanthine, xanthine and uric acid from other plasma components. Due to minimal sample preparation using the centrifugal membrane filter, the ideal HPLC column should have high efficiency for resolving inosine and hypoxanthine components from components in the plasma matrix. Conventional HPLC columns such as Synergi Polar-RP $C_{18}$ (15 cm×3.0 mm I.D.×4 μm packing) and Hypersil ODS $C_{18}$ (15 cm×3.2 mm I.D.×3 μm packing) were evaluated versus the recently marketed HPLC column technology, the Onyx monolithic $C_{18}$ column (10 cm×4.6 mm I.D.). The monolithic column provided superior chromatographic resolution of components with a low system backpressure of approximately 84 bar (gradient time zero conditions and flow rate of 1 mL/min). It should be emphasized that both conventional HPLC columns were evaluated at operating flow rates of ~0.6 mL/min and with system pressures that were approximately twice as high as when using the monolithic column. The supplier of the monolithic column cited advantages of high component efficiencies (resolution) and low system backpressure with use of the new monolithic column technology. We observed that both of these stated advantages over the two conventional mid-bore diameter HPLC columns evaluated were clearly demonstrated.

The mobile phase aqueous component, 0.1% TFA in deionized water, provided a pH of 2.2 which also provided good peak shape (e.g. uric acid component, pKa ~5.8) from components of interest from the endogenous plasma components (MW<10,000 Da) obtained from the YM-10 sample preparation. Optimization and adjustment of the acid strength improved the separation between hypoxanthine (RT 5.2 min) and uric acid (RT 5.7 min). Initial use of aqueous 0.05% TFA did not provide component baseline resolution while aqueous 0.1% TFA offered complete component baseline resolution at the expense of increased column retention times. The mobile phase organic modifiers (e.g. acetonitrile versus methanol) were evaluated to determine which organic solvent would provide the best chromatographic separation from endogenous plasma components and at the same time being most cost effective. Methanol was chosen as the organic modifier as it provided symmetrical component peak shapes and good selectivity from other endogenous plasma components; however the HPLC system backpressure was somewhat higher when using methanol with the methanol gradient increasing from 1 to 90%. Methanol is also more cost effective for routine HPLC analysis because of its lower procurement cost.

A mobile phase gradient was used for reproducible separations of the structurally similar purines (hypoxanthine, uric acid) and nucleosides (inosine, adenosine). Since the mobile phase organic constituent is critical to controlling component elution times (initial 1% methanol composition at gradient time zero), the use of protein precipitation technique using solvents such as acetonitrile or methanol (typically 1:1 or 2:1, organic:plasma ratio) was eliminated from consideration. The structurally similar components injected using organic solvent precipitation were not chromatographically resolved due to band broadening effects from the added organic modifier. Different column oven temperatures (e.g. ambient lab of 20, 30 and 40° C.) were evaluated without significant chromatographic improvement (component resolution, peak shape), thus ambient temperature was utilized for the analysis. At higher column temperatures (e.g. 40° C.), component co-elution for both early (hypoxanthine, uric acid) and late components (inosine, adenosine) was observed.

Linearity, Limits of Quantitation and Detection, Computations

The plasma method was linear throughout the concentration range of 0.25-5 μg/mL for inosine (mean correlation coefficient of 0.9991, n=10) and hypoxanthine (mean correlation coefficient of 0.9998, n=10) with all standard back-calculated values within 5% of their nominal amount. The limit of detection (LOD) for each component of the method was ~100 ng/mL. The LOD was determined using a fortified amount of each component in pooled blood blank plasma at 100 ng/mL (n=3) and calculation from each component's standard curve (component peak heights had greater than three times s/n than blank plasma background). For plasma component calculations and reporting results, normal linear regression utilizing external standardization and peak height was used with the lowest standard calibrator (0.25 μg/mL) used as the limit of quantitation (defined as combined accuracy and precision within 20% of the nominal amount).

Accuracy, Precision and Recovery

The accuracy and precision for the method was determined by evaluation of replicate prepared plasma control samples at 250, 2000 and 4000 ng/mL (Table 3). The combined intra-day (within day) and inter-day (between day) accuracy of the method was reported as the percent error of nominal fortified amounts versus measured component concentrations. The combined intra-day and inter-day precision of the method was reported as percent relative standard deviation (% R.S.D.). The method demonstrated excellent accuracy (±6%) and precision (±8.1) for both components in plasma (n=15 at each component concentration level).

TABLE 3

Combined intra- and inter-day accuracy and precision for inosine and hypoxanthine in plasma controls

| Component | Fortified concentration (ng/mL) (n = 15) | Calculated mean concentration (ng/mL) (n = 15) | Error (%) | R.S.D. (%) |
|---|---|---|---|---|
| Inosine | 250 | 243 | −2.8 | 8.1 |
| Inosine | 2000 | 1966 | −1.7 | 4.9 |
| Inosine | 4000 | 3914 | −2.2 | 3.6 |
| Hypoxanthine | 250 | 265 | 6.0 | 7.5 |
| Hypoxanthine | 2000 | 2044 | 2.2 | 5.5 |
| Hypoxanthine | 4000 | 3931 | −1.7 | 2.2 |

Controls demonstrated excellent accuracy ±6% and precision ±8.1% throughout the plasma concentration range.

Absolute recovery for the plasma method was evaluated by comparing extracted fortified controls prepared in pooled blood blank plasma versus unextracted standards prepared in deionized water (n=3 at 250, 2000 and 4000 ng/mL). The absolute recovery for the plasma method was determined to be >98% for both inosine and hypoxanthine. In addition, the standards and controls used for all HPLC analysis were prepared and handled identical to patient and volunteer subject samples, thus controlling for potential errors in sample handling, micropipetting and YM-10 component extraction recovery.

Chromatography

FIGS. 4 A-E illustrate chromatograms of 2000 ng/mL hypoxanthine (RT ~5.3 min), uric acid (RT ~5.8 min), xanthine (RT ~7.2 min), adenosine (RT ~10.7 min) and inosine (RT ~10.9 min) in deionized water for marking component retention times; limit of quantitation and lowest plasma standard of 250 ng/mL hypoxanthine and inosine; pooled blank plasma from the VCU Health Systems Hospital blood bank; prepared plasma from a healthy female subject; and prepared plasma from a hospital emergency room female patient exhibiting symptoms of chest pain and acute myocardial ischemia (FIG. 4 A, B, C, D and E, respectively). The method demonstrated excellent chromatographic selectivity with no endogenous plasma interferences at the retention times of hypoxanthine and inosine with sufficient sensitivity for both components of interest using conventional UV detection and an analytical run time of ~21 min (allows mobile phase gradient equilibration). To extend column lifetime, the analytical column was flushed after each analytical run (~50 injections) for 1 h at 1.0 mL/min with acetonitrile: deionized water (90:10, v/v) to eliminate potential retained nonpolar substances from the column.

Sample Preparation, Optimization and Filtrate Stability

Sample preparation evaluations using protein precipitation and centrifugal membrane filters were conducted. As previously described, organic solvent precipitation was not useful due to resulting poor chromatographic resolution of structurally similar components. TCA was not evaluated due to the hazards of using the strong acid and the resulting sample dilution effect potentially affecting overall method sensitivity. The centrifugal membrane filter is commonly used to concentrate peptides, proteins and nucleic acids for proteomic and genomic determinations [25]. Since the molecular weights of our components are all less than 300 Da, our approach to using this technique was to inject the filtrate which would contain the low molecular weight components that transfers across the YM-3 or YM-10 cellulose membrane cutoff filters. This essentially removes most peptides and all proteins from the sample to be injected as they are retained by the cellulose membrane cutoff filter, thus improving method selectivity. Method sensitivity is also improved because there is no sample dilution effect since no solvent is added.

Evaluations to optimize sample preparation conditions using the YM-10 (10,000 Da MWCO) and YM-3 (3000 Da MWCO) centrifugal filter were conducted. With the centrifugal force set at 14,000×g (recommended by YM-10 supplier) and using 250 µL of prepared plasma control samples, the centrifuge spin time was varied from 5, 15, 30 and 60 min. The 5 min spin time did not provide enough time to adequately separate plasma proteins from the aqueous matrix (salts, small peptides and substances less than 10,000 Da) with an insufficient amount of sample filtrate recovered. The 15, 30 and 60 min centrifugal spin times resulted in maximum recovery of sample filtrate. However, the 60 min spin filtrate samples were significantly warmer than ambient lab temperature most likely due to warming effects of the sample tubes friction with air from the centrifugal spin. Thus to eliminate potential component degradation due to heat from spinning 60 min and to shorten sample preparation time, a spin time of 15 min was used for all analyses as above.

Results for the YM-3 filter evaluation demonstrated longer spin times were required (~45-60 min) at 14,000×g versus the 15 min spin using the YM-10 filter. The YM-3 filtrate did not offer better filtration of smaller plasma peptides (<10K Da), as observed on chromatograms, than was already achieved using the YM-10 filter. However, using either YM-3 or YM-10 filter effectively removed the purine nucleoside phosphorylase enzyme (nominal weight ~90-94 kDa protein, [26,27]) thus eliminating the potential for inosine to hypoxanthine metabolism in the sample filtrate. The filtrates were stored frozen (−70° C.) after HPLC analysis with both inosine and hypoxanthine components demonstrating stability for greater than 3 months.

Plasma Purine Nucleoside Phosphorylase Activity

Purine nucleoside phosphorylase (PNP, EC 2.4.2.1) is an enzyme that rapidly metabolizes inosine to hypoxanthine in blood (t½<5 min due to red blood cells). This enzyme has low activity in plasma and is normally found in human cardiac muscle, GI tract, spleen, brain and red blood cells [28,29]. Therefore, to better estimate an ischemic heart's effluxed inosine during periods of acute cardiac oxidative stress, venous blood samples should be kept cold (ice) and prepared immediately. Either the blood sample should be immediately inhibited (e.g. peldesine, competitive inhibitor [28]) or the metabolite hypoxanthine should be simultaneously determined with inosine to better estimate the level of acute cardiac ischemia. In whole blood or plasma samples, hypoxanthine will not be further metabolized to xanthine as the human enzyme xanthine oxidase (XO), which is required for hypoxanthine to xanthine conversion, has low activity in plasma [30] and being typically found in human tissue (liver, small intestine) and other bodily fluids (milk, colostrum). A plasma (heparinized) sample is recommended for inosine and hypoxanthine determination in that the approximate 30 min clot time required for a serum sample would allow significant conversion of inosine to hypoxanthine in the collection tube, which would contain PNP from the red blood cell and plasma matrix.

Figure 5:
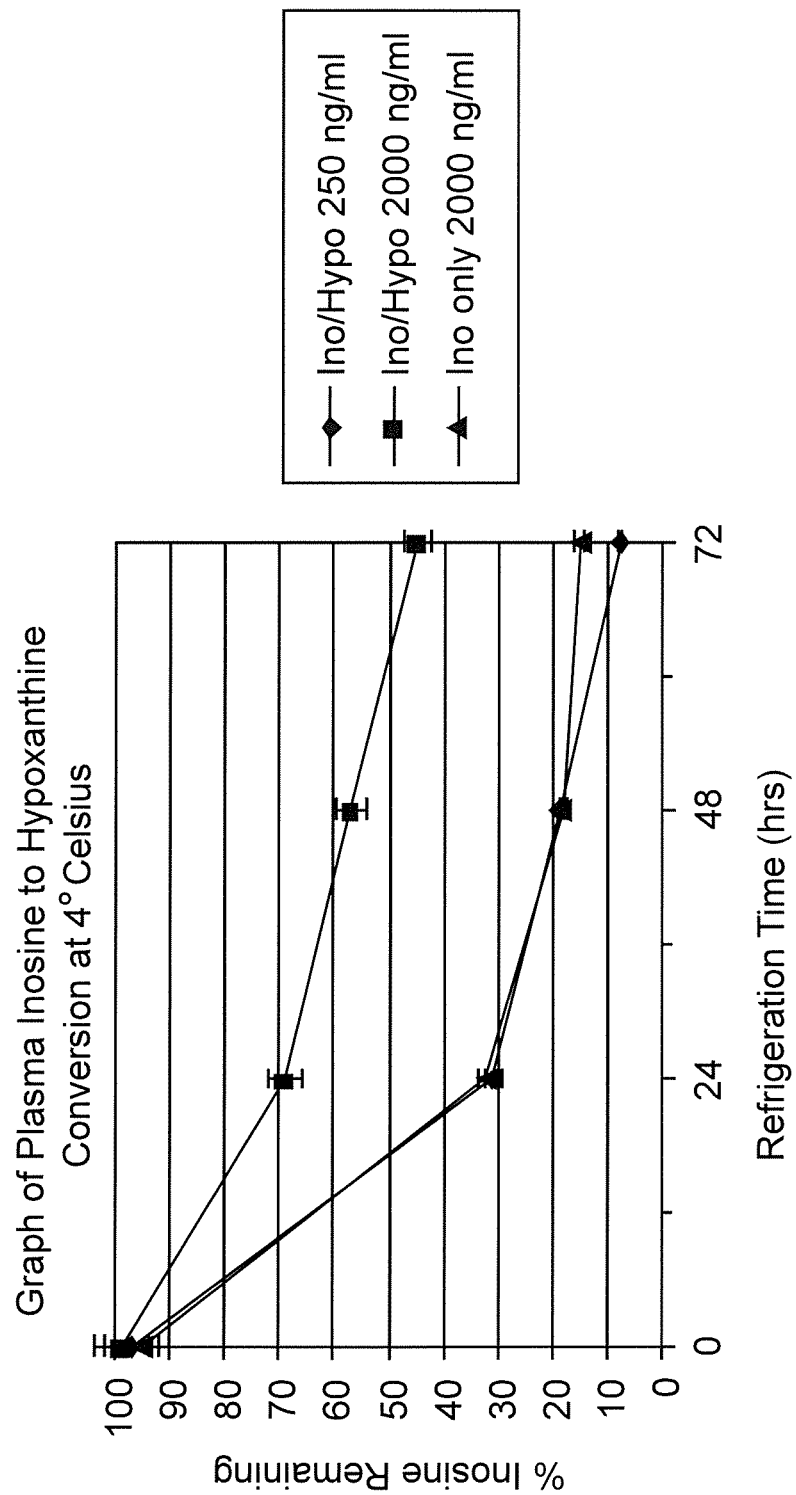
FIG. 5. Graph of mean percent inosine remaining after plasma PNP metabolism when stored at 4° C. Square symbols represent fortified amounts of 2000 ng/mL of inosine and hypoxanthine in blank plasma (n=3), diamond symbols represent fortified amounts of 250 ng/mL of inosine and hypoxanthine in blank plasma (n=3) and triangle symbols represent fortified amount of 2000 ng/mL inosine only in blank plasma (n=3).

Several evaluations (n=3 samples at each condition) were performed to evaluate inosine metabolism by PNP activity in plasma stored at 4° C. (refrigerator), −20 and −70° C. Results of the 4° C. evaluation can be seen in FIG. 5; plasma fortified with inosine only at 2000 ng/mL and without PNP enzyme inhibitor is metabolized rapidly to hypoxanthine (~70% in 24 h); plasma fortified with 250 ng/mL of inosine and hypoxanthine and without PNP enzyme inhibitor is also metabolized rapidly to hypoxanthine (~70% in 24 h); however the plasma fortified with 2000 ng/mL of inosine and hypoxanthine and without a PNP enzyme inhibitor, is metabolized less rapidly to hypoxanthine (~30% in 24 h) and slightly less than 50% after 72 h. Results of storing fortified plasma samples at −20° C. immediately after preparation indicated a reduced rate of inosine to hypoxanthine conversion (~30% after 8 months) with storage at −70° C. almost completely deactivating the PNP enzyme (<5% inosine conversion after 3 months).

A possible explanation for the plasma hypoxanthine concentration dependence for the conversion rate of inosine to hypoxanthine would be product inhibition (PNP $K_{eq}$ ~0.04 mM) [31]. This low Keq indicates that thermodynamically, inosine synthesis is favored over product conversion to hypoxanthine. When the venous sample plasma concentration of hypoxanthine is present at higher levels (e.g. 2000 ng/mL), the conversion of inosine to hypoxanthine by plasma PNP decreases in the absence of significant XO enzyme activity, which converts hypoxanthine to xanthine and uric acid for biological elimination (therefore XO activity ultimately increases PNP activity as it reduces hypoxanthine product inhibition of PNP). It was also determined that the total amount of inosine and hypoxanthine fortified into the pooled plasma was recovered, thus verifying the lack of significant XO activity in human plasma and supports our recommendation of simultaneous determination of both inosine and hypoxanthine components. A preliminary investigation to show the utility of the method is shown in FIG. 1D (healthy control with 350 ng/mL inosine and 373 ng/mL hypoxanthine) and 1E (potential acute cardiac ischemia patient with 641 ng/mL inosine and 3987 ng/mL hypoxanthine). These figures demonstrate an increase in both inosine and hypoxanthine concentrations in one patient having presented with chest pain and undergoing evaluation for acute cardiac ischemia.

Conclusions

A sensitive and selective method has been developed for evaluation of inosine and hypoxanthine in human plasma. The method employed a one-step sample preparation for plasma (no organic solvents or solid phase extraction cartridges required) with high analyte recoveries, which eliminated the need for an internal standard. In addition, this method utilized recently introduced HPLC monolithic column technology, which provided sufficient selectivity and sensitivity for measurement of these components. The method was employed without significant methodological problems in the evaluation of plasma samples obtained from healthy volunteers and hospital emergency room patients presenting with chest pain and potential acute myocardial ischemia.

References for Example 2

[1] World Health Organization, The Atlas of Heart Disease and Stroke, 2002 Cardiovascular Mortality Statistics, website located at www.who.int/cardiovascular diseases [internet, 16 Oct. 2006].
[2] Evaluation of Technologies for Identifying Acute Cardiac Ischemia in Emergency Departments. Summary, Evidence Report/Technology Assessment: Number 26, AHRQ Publication 00-E031 (2000), Agency for Healthcare Research and Quality, Rockville, Md., USA.
[3] T. Domer, A. Rieder, Wien. Med. Wochenschr. 154 (11-12) (2004) 257.
[4] K. Okrainec, D. K. Banerjee, M. J. Eisenburg, Am. Heart J. 148 (1) (2004) 7.
[5] A. Naudziunas, L. Jankauskiene, E. Kalinauskiene, V. Pilvinis, Prev. Med. 41 (2) (2005) 570.
[6] K. Beyerle, Nurs. Manage. 33 (9) (2002) 37.
[7] G. P. Young, T. R. Green, Am. J. Emerg. Med. 11 (5) (1993) 444.
[8] A.D.A.M. Inc., Heart Attack and Acute Coronary Syndrome. Available from website located at adam.about.com/reports/000012 4.htm.
[9] D. M. Bunk, J. J. Dalluge, M. J. Welch, Anal. Biochem. 284 (2000) 191.
[10] B. M. Mayr, O. Kohlbacher, K. Reinert, M. Sturm, C. Gropl, E. Lange, C. Klein, C. G. Huber, J. Proteome Res. 5 (2006) 414.
[11] F. S. Apple, R. H. Christenson, R. Valdes Jr., A. J. Andriak, A. Berg, S. Duh, Y. Feng, S. A. Jortani, N. A. Johnson, B. Koplen, K. Mascotti, A. H. Wu, Clin. Chem. 45 (2) (1999) 199.
[12] C. Heeschen, B. U. Goldmann, L. Langenbrink, G. Matschuck, C. W. Hamm, Clin. Chem. 45 (10) (1999) 1789.
[13] F. S. Apple, F. P. Anderson, P. Collinson, R. L. Jesse, M. C. Kontos, M. A. Levitt, E. A. Miller, M. M. Murakami, Clin. Chem. 46 (10) (2000) 1604.
[14] J. McCord, R. M. Nowak, P. A. Mcculloguh, C. Foreback, S. Borzak, G. Trokarski, M. C. Tomlanovich, G. Jacobsen, W. D. Weaver, Circulation 104 (2001) 1483.
[15] J. D. Feng, P. K. Yeung, Ther. Drug Monit. 22 (2) (2000) 177.
[16] D. Farthing, L. Xi, L. Gehr, D. Sica, T. Lams, H. T. Karnes, Biomarkers 11 (5) (2006) 449.
[17] R. Boulieu, C. Bory, P. Baltassat, P. Divry, Clin. Chim. Acta 142 (1984) 83.
[18] R. Boulieu, C. Bow, P. Baltassat, C. Gonnet, Anal. Biochem. 129 (1983) 398.
[19] M. D. Scott, L. J. Baudendistel, T. E. Dahms, J. Chromatogr. 576 (1) (1992) 149.
[20] W. Furst, S. Hallstrom, J. Chromatogr. 578 (1) (1992) 39.
[21] B. Tavazzi, G. Lazzarino, P. Leione, A. M. Amorini, F. Bellia, C. G. Janson, P. V. Di, L. Ceccarelli, S. Donzelli, J. S. Francis, B. Giardina, Clin. Biochem. 38 (11) (2005) 997.
[22] C. M. Jabs, P. Neglen, B. Eklof, E. J. Thomas, Clin. Chem. 36 (1) (1990) 81.
[23] G. Severini, L. M. Allberti, Clin. Chem. 33 (12) (1987) 2278.
[24] Phenomenex Inc., website located at www.phenomenex.com/phen/products/onyx/index.htm.
[25] Microcon® Centrifugal Filter Devices [PDF data sheet July 1998], Millipore Corp., Bedford, Mass., USA.
[26] W. J. Cook, S. E. Ealick, C. E. Bugg, J. D. Stoeckler, R. E. Parks Jr., J. Biol. Chem. 256 (8) (1981) 4079.
[27] W. R. Osborne, J. Biol. Chem. 255 (15) (1980) 7089.
[28] T. X. Viegas, G. A. Omura, R. R. Stoltz, J. Kisick, J. Clin. Pharmacol. 40 (2000) 410.
[29] T. Yamamoto, Y. Moriwaki, S. Takahashi, Y. Nasako, J. Yamakita, K. Hiroishi, K. Higashino, Anal. Biochem. 227 (1995) 135.
[30] T. Yamamoto, Y. Moriwaki, S. Takahashi, Z. Tsutsumi, J. Yamakita, Y. Nasako, K. Hiroishi, K. Higashino, J. Chromatogr. B 681 (1996) 395.
[31] Brenda Enzyme Database, Institute of Biochemistry, University of Cologne, Germany, website located at www-.brenda.uni-koeln.de.

Example 3

Rapid Chemiluminescence Detection of Inosine and Hypoxanthine Using Microplate Luminometer Introduction This Example describes the development of a rapid chemiluminescence test method for determination of inosine and hypoxanthine in human plasma. The purpose is to allow for rapid patient screening capability (diagnostic tool for acute cardiac ischemia) for potential use, for example, in hospital emergency department environments. The luminescence method was tested on samples from healthy individuals and hospital patients with confirmed acute MI (hospital documented elevated levels of cTnT). The method is rapid (defined as less than 10 minute analysis time), sensitive and specific for inosine and hypoxanthinem thereby reducing potential errors in interpreting sample test results (e.g. false positive and false negative results are minimized). Currently, there are no rapid test methods to determine inosine and hypoxanthine in plasma, which can meet the stringent sample turnaround time requirements of an emergency medical services (EMS) environment. The rationale for using chemiluminescence technology over commonly used liquid chromatography (LC) and immunoassay technologies are as follows: LC and immunoassay methods are both very sensitive and specific techniques (e.g. monoclonal antibodies for immunoassay and mass spectrometer detection for LC); however, an LC-MS system is expensive to purchase and operate, both techniques require technical expertise to perform, and both lack the rapid turnaround time needed by an EMS facility analyzing a priority "stat" type samples. However, a luminometer can measure chemiluminescent light, is relatively inexpensive to purchase, currently used in clinical labs (microplate capability), and can provide high component sensitivity.

Luminescence technology is well established with many instrument vendors (e.g. BMG LabTek Inc. Lumistar Optima (Durham, N.C., USA), BioTek Synergy HT (Winooski, Vt., USA), Thermo Fisher Scientific Luminoskan (Waltham, Mass., USA)) and suppliers (e.g. Corning Life Sciences, Lowell, Mass., USA) of luminescence supplies and reagents available worldwide. It is known to be one of the most sensitive techniques, with one recent publication, for example, on its application for low ng/ml concentrations of ATP in human plasma [Gorman et al., 2007]. The high sensitivity of luminescence is primarily due to its high analyte signal to noise (s/n) ratio, with reported detection levels at low picogram and femtogram levels.

Figure 6:
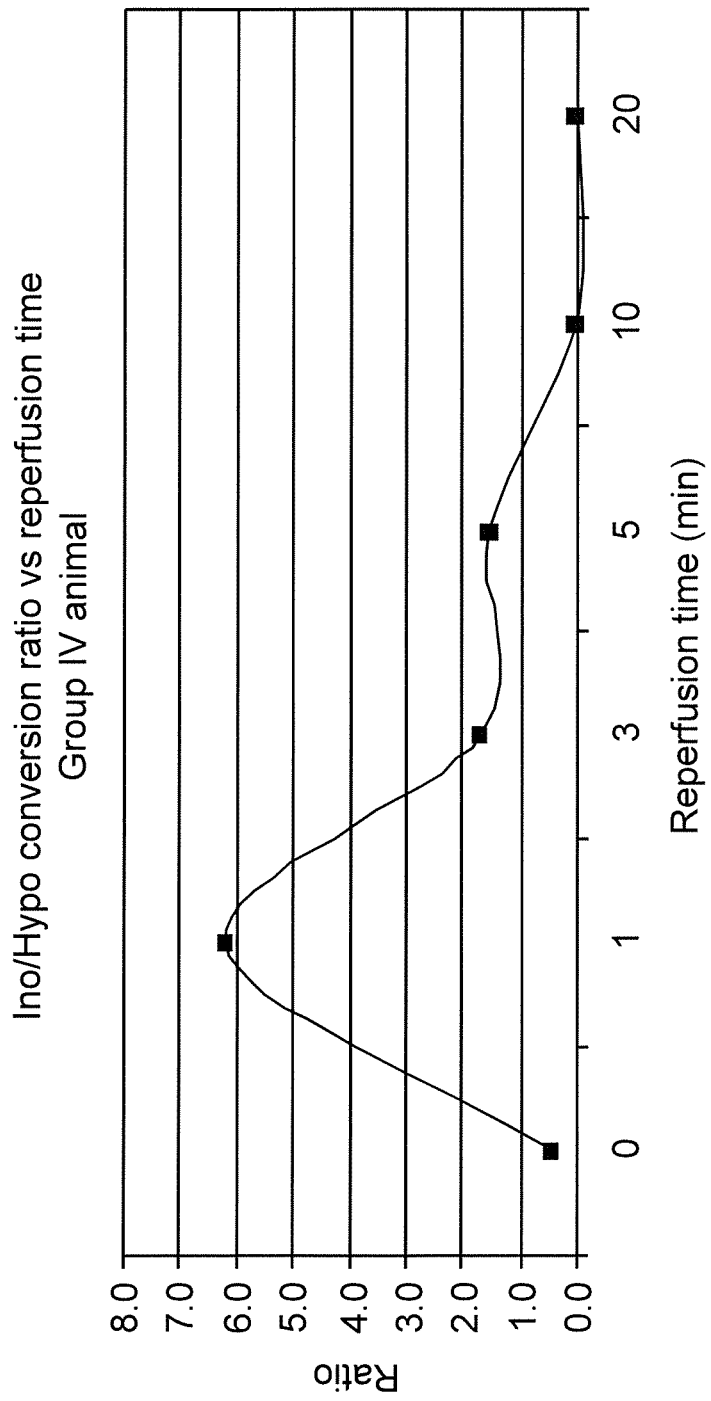
FIG. 6. Plot of inosine [µM] to hypoxanthine [µM] (ino/hypo) conversion ratio versus reperfusion time (min). The plot represents data from one animal heart preparation in group Group IV to 1 mM SA and ischemic experimental conditions. Ino/hypo conversion ratio is highest in the 1 min reperfusion sample and returns to a constant ratio before dropping to zero as aerobic conditions presumably deactivate ADA and PNP enzymes in the cardiac myocytes.

To address biomarker specificity requirement, the subject luminescence test method will utilize biological enzymes purine nucleoside phosphorylase (PNP) and xanthine oxidase (XO), which are specific for enzymatic conversions of inosine and hypoxanthine, respectively. The PNP enzyme converts inosine to hypoxanthine and XO converts hypoxanthine to xanthine, followed by XO conversion of xanthine to final product uric acid (in human species). Each time XO reacts with one mole of hypoxanthine, and subsequently with one mole of xanthine, the metabolic by-products of each XO enzymatic turnover is the production of one mole of hydrogen peroxide and two moles of superoxide anion radical ($O^2-$). Both of these by-products can become substrates for luminescence type reactions. Several commonly used luminescent materials (e.g. luminol (oxidation), lucigenin (reduction), and PHOLASIN® (oxidation) were considered for this research. If using luminol or lucigenin as the luminescent material, the hydrogen peroxide (which has both oxidizing and reducing capabilities) can react with the horseradish peroxidase (HRP) enzyme, luminol, and signal enhancers to generate measurable blue light ~450 nm, thus an amplification of signal effect (one mole of hypoxanthine and xanthine can generate two moles of hydrogen peroxide) (FIG. 6).

However, to achieve even greater sensitivity at low concentrations (ng/ml or μM levels of inosine and hypoxanthine are typically found in human plasma) another luminescence approach was investigated, which utilizes a highly sensitive photoprotein (PHOLASIN®). Since one mole of hypoxanthine will generate 4 moles of superoxide anion radicals (SAR) as a by-product of XO activity, using a chemiluminescent material that reacts with SAR should theoretically provide even more luminescence signal, thus potentially increasing the sensitivity two fold over using the hydrogen peroxide/horseradish peroxidase/luminol approach. One article cited PHOLASIN® having more than 100 fold sensitivity than lucigenin (Knight, 1997).

Figure 7:
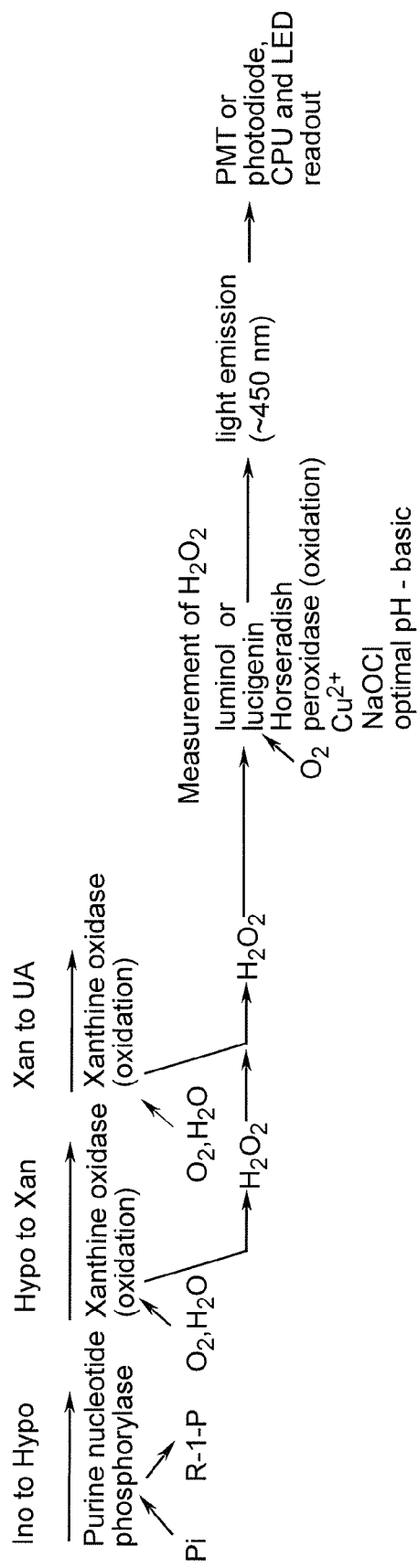
FIG. 7. Diagram of enzymatic conversions of inosine and hypoxanthine components with generation of hydrogen peroxide as a by-product, which can react with luminol or lucigenin and HRP to generate visible blue light (chemiluminescence).
Figure 8:
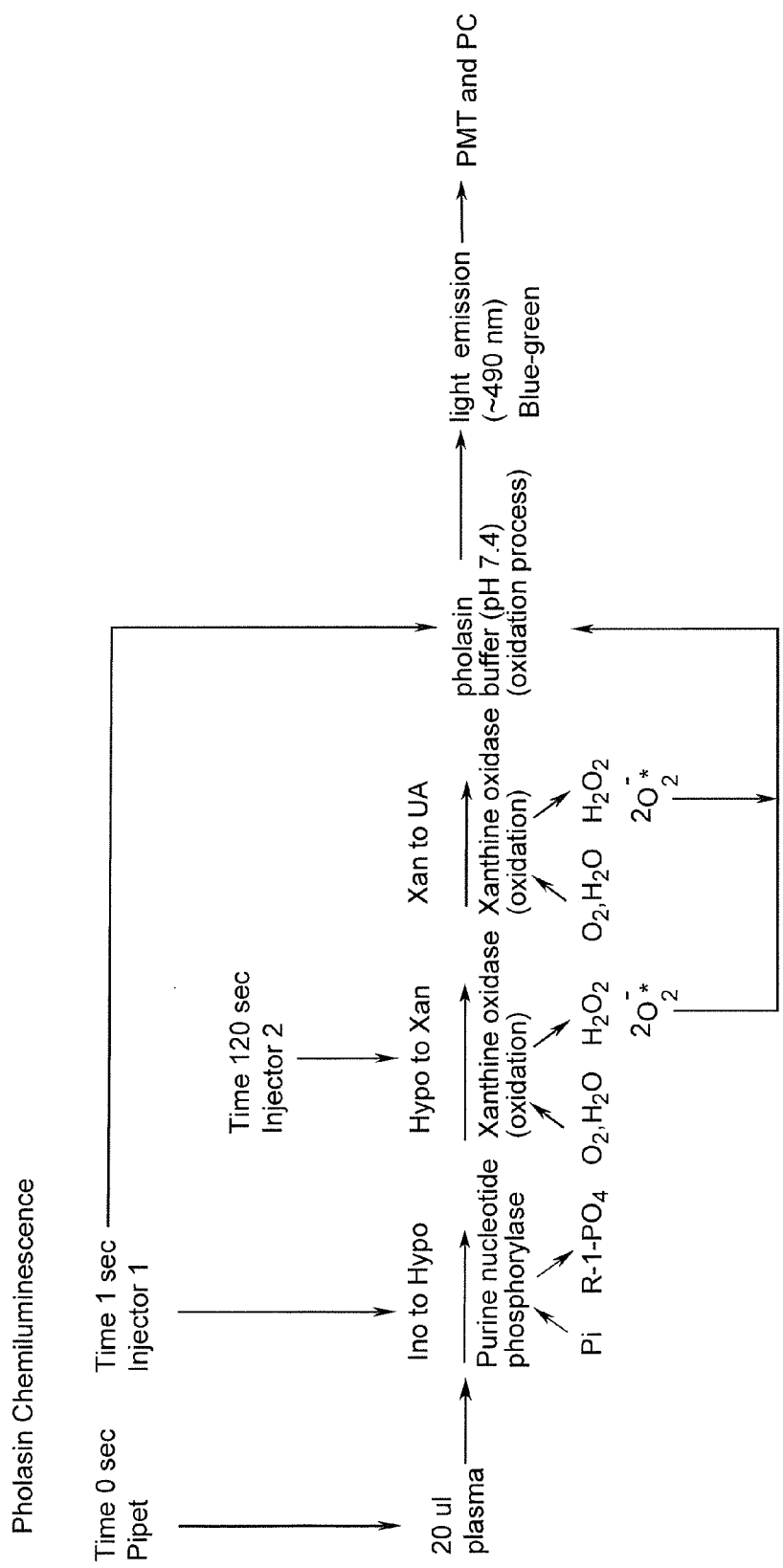
FIG. 8. Diagram of typical reagent addition, injector time points and resulting PHOLASIN® emission (chemiluminescence).

PHOLASIN®, a photoprotein isolated from the bi-valve mollusk, has been reported to be a very sensitive chemiluminescent material (called Lucidalin®) for SAR and other reactive oxygen species (ROS) such as the hydroxyl free radical (Knight, 1988). PHOLASIN® has been extensively studied and patented by Knight Scientific, Plymouth, UK. It is an approximately 34-36 kDa glycoprotein, which can be made excitable by several ROS, emitting blue-green light, and it has been reported to not have fluorescent properties. The presence of SAR can react with the PHOLASIN® photoprotein to generate measurable light (~490 nm) (FIG. 7), thus an amplification of signal effect (one mole of hypoxanthine can generate four moles of SAR), which should increase sensitivity and provide lower component detection limits. The reaction of PHOLASIN® with SAR can be very quick (flash type technique, typically seconds) and may be made even more sensitive with use of signal enhancers (e.g. Adjuvant-k (proprietary) from Knight Scientific).

The Lumistar Optima Microplate Reader (BMG LabTech, Durham, N.C., USA) was used for all luminescence evaluations. The instrument has temperature control, supports the use of 96 well plates (opaque white) which were purchased from Corning Life Sciences (Lowell, Mass., USA), and is capable of variable microplate mixing speeds with flash and glow luminescence capabilities. The instrument is fitted with two direct injectors capable of rapid injections (e.g. 310 μl/sec), thus micropipetting assay reagents into the sample wells was automatically performed, which may help to reduce potential errors from manual pipetting.

Experimental

Chemicals, Reagents and Materials

Hypoxanthine, xanthine and ethyl alcohol (HPLC grade, denatured) were purchased from Acros Organics (Fair Lawn, N.J., USA). Inosine, dibasic sodium hydrogen phosphate, and uric acid were purchased from Sigma-Aldrich (St. Louis, Mo., USA). Enzymes xanthine oxidase (isolated from bovine milk, Grade III, ammonium sulfate suspension, enzymatic activity ~1.3 units/mg protein, storage temp 2-8° C.), purine nucleoside phosphorylase (isolated from human blood, lyophilized powder, enzymatic activity ~19 units/mg protein, storage −20° C.) and uricase (isolated from *Arthrobacter globiformis*, lyophilized powder, ~19.7 units/mg protein, storage −20° C.) were all purchased from Sigma-Aldrich.

A commercial test kit used for antioxidant evaluations was purchased for initial setup of the luminometer and included an assay utilizing xanthine/xanthine oxidase plate mode kinetics (glow technique). The kit included PHOLASIN® (50 μg), xanthine, xanthine oxidase [10.25 mU/ml] and buffer (proprietary) for plate mode kinetics and was purchased from Knight Scientific (Plymouth, UK). The luminometer instrument was qualified using the commercial antioxidant test kit and by successful replication of the xanthine/xanthine oxidase plate mode kinetics profile from Knight Scientific. For all experiments following instrument qualification, the reagents and enzyme solutions were prepared accordingly. Dibasic sodium hydrogen phosphate was used to prepare the 20 mM assay buffer solution with ultrapure deionized water as the diluent (final pH 7.4 using concentrated phosphoric acid). Ultrapure deionized water (~18 MO-cm) used for all reagent solutions was filtered (0.2 μm) prior to use.

The luminometer rinse solution for the direct injector syringes was prepared using ethyl alcohol:deionized water mixture (75:25%, v/v). Weekly rinses were performed to reduce potential material (e.g. protein and enzyme residue) buildup in the syringes, reagent tubing and injector needles. Opaque 96 well microplates were purchased from Corning Life Sciences (Lowell, Mass., USA) and stored in the dark at ambient temperature. Blank human plasma (lithium anticoagulant) from one healthy volunteer (250 ml), an additional six healthy volunteers plasma (lithium heparin) samples (1 ml each), and six patient's plasma (lithium heparin) samples with confirmed acute MI (hospital reported elevated cTnT, 1 ml each) were purchased from ProMedDx (Norton, Mass., USA) and stored at −20° C. prior to use.

Preparation of Standards, Enzymes and PHOLASIN® Solutions

Stock standards of inosine (25 μg/ml, 93.2 μM), hypoxanthine (25 μg/ml, 183.7 μM), xanthine (25 μg/ml, 164.4 μM) and uric acid (25 μg/ml, 148.7 μM) were prepared in deionized water, stored at 4° C. with stability greater than 3 months. Working calibration standards for each component were prepared in deionized water immediately prior to use. For experiments, the working xanthine oxidase solution was prepared by pipetting 40 μL of the aqueous stock XO (from bovine milk) suspension into 2.0 ml of assay buffer (pH 7.4) resulting in ~676 mU XO/ml. The working XO solution was stable at ambient laboratory temperature (22° C.) and could be stored at 4° C. overnight with minimal loss in enzyme activity; however the working XO solution should not be stored frozen (e.g. −20° C.), as a complete loss of enzyme activity was observed upon freeze-thaw and subsequent use.

To prepare PNP and uricase solutions from solid and lyophilized purine nucleoside phosphorylase and uricase, 1.0 ml of assay buffer (pH 7.4) was pipetted directly into the vendor container bottle with gentle vortexing into solution. After reconstitution using 1 ml of assay buffer (pH 7.4), the PNP stock concentration was ~18.7 Units PNP/ml and uricase stock concentration was ~110 Units uricase/ml. A working solution of PNP [~701 mU PNP/ml] was prepared by pipetting 75 µl of the aqueous stock material into 2.0 ml of assay buffer (pH 7.4). A working solution of uricase [~1.1 U uricase/ml] was prepared by pipetting 20 µL of the aqueous stock material into 2.0 ml of assay buffer (pH 7.4). Both working solutions of PNP and uricase were stable at ambient laboratory temperature and could be stored at 4° C. overnight with minimal loss in enzyme activity.

For preparation of the PHOLASIN® luminescent material, 5.0 ml of assay buffer (pH 7.4) was pipetted directly into the vendor container bottle containing 50 µg PHOLASIN® with gentle vortexing, resulting in a ~10 µg/ml solution. The prepared PHOLASIN® reagent was stable at ambient laboratory temperature and 4° C., and was stored protected from light to eliminate potential basal luminescence as it is an excitable photoprotein. The reconstituted PHOLASIN® solution was transferred and stored in plastic screw top tubes (~1 ml aliquots stored at −20° C.).

Luminometer Equipment and Set Points

The luminometer equipment consisted of a BMG LabTech Inc. Lumistar Optima and Optima software (version 2.1) (Durham, N.C., USA) and Dell Optiplex 745 PC (Dell, Tex., USA). The luminometer was equipped with temperature control (8° C. to 45° C.), two direct injectors (minimum injection volume of 3 µl) with variable injection speeds (100 µl/s to 420 µl/s), and microplate shaking (orbital, linear, figure eight) capability. The luminometer listed specifications for the limit of detection (<50 amol/well ATP), spectral range (240-740 nm) and dynamic range (9 decades). All luminescence assays utilized opaque 96 well plates, an incubation temperature of 25° C., lens mode (no emission filter) and a photo-multiplier (PMT) gain setting of 3900 volts. Equipment set points for all experiments in the flash mode are listed in FIG. 9.

Method Development and Optimization

Development and optimization of the luminescence test method included evaluation of parameters such as determining hypoxanthine concentration level range, adjustment of XO enzyme concentration level to reduce analysis time, and enzyme incubation time (e.g. PNP) to maximize sensitivity and repeatability and to minimize turnaround time (<10 min analysis). All plasma analysis utilized 20 µl of sample in a final microplate well volume of 200 µl (effectively making a 1:10 dilution of the plasma sample). Potential endogenous interference (e.g. uric acid) was evaluated to determine quenching effects as this substance has antioxidant capacity and is typically found in plasma at high concentrations (e.g. 350-450 µM), especially in gout patients.

The HPLC results from normal volunteers (ProMedDx plasma) and non-traumatic chest pain patients (Chippenham Hospital ED plasma) were used to estimate expected plasma concentrations of inosine and hypoxanthine (Table 4). Since the luminometer is a detection device and will not separate a mixture of components (as does HPLC), it was necessary to utilize the PNP enzyme and convert component inosine to hypoxanthine, and then measure the resulting total plasma hypoxanthine (inosine plus hypoxanthine) concentration. Using the XO enzyme, hypoxanthine converts to xanthine, and xanthine to uric acid. The luminometer measures the light signal generated from the XO reaction with hypoxanthine and xanthine (XO generates superoxide anion radicals which react with the luminescent material PHOLASIN®). Using a µg/ml to µM (micro molar) conversion table (Excel formula computations, Table 5), a standard curve of hypoxanthine was prepared at concentration range of 2.3 to 30.3 µM. The initial hypoxanthine concentration range was set to focus on hypoxanthine concentrations to maximize the luminescence method sensitivity and detect concentration differences between healthy normal individuals and non-traumatic chest pain patients (e.g. ~3 µM for normal individual and ~15 µM for lowest observed chest pain patient). Plasma samples above the highest standard can be diluted with deionized water. The initial range incorporated total inosine and hypoxanthine concentrations from both healthy normal individuals and non-traumatic chest pain patients (based on n=20 for each group).

TABLE 4

Estimated inosine, hypoxanthine, xanthine and uric acid concentrations in healthy normal individuals and non-traumatic chest pain patients.

|  | Plasma [ug/mL] | Plasma [uM] | Comments |
| --- | --- | --- | --- |
| Estimated lowest inosine level | 0.10 | 0.4 |  |
| Estimated lowest hypoxanthine level | 0.10 | 0.7 |  |
| Assume 100% inosine to hypoxanthine conversion |  | 1.1 |  |
| Estimated (normals) inosine level | 0.30 | 1.1 |  |
| Estimated (normals) hypoxanthine level | 0.30 | 2.2 |  |
| Assume 100% inosine to hypoxanthine conversion |  | 3.3 | Estimated levels (normals) from Feng et al, Ther Drug Mon (2000) 22: 177-183. |
| Estimated (ischemic) inosine level | 0.3 | 1.1 | Lowest chest pain patient value |
| Estimated (ischemic) hypoxanthine level | 2.0 | 14.7 |  |
| Assume 100% inosine to hypoxanthine conversion |  | 15.8 | Ischemic (based on Chippenham ED data). |
| Estimated (ischemic) inosine level | 7.8 | 29.1 | Highest chest pain patient value |
| Estimated (ischemic) hypoxanthine level | 9.7 | 71.3 |  |

TABLE 4-continued

Estimated inosine, hypoxanthine, xanthine and uric acid concentrations in healthy normal individuals and non-traumatic chest pain patients.

| | Plasma [ug/mL] | Plasma [uM] | Comments |
|---|---|---|---|
| Assume 100% inosine to hypoxanthine conversion | | 100.3 | Ischemic (based on Chippenham ED data). |
| Estimated (normals) xanthine level | 0.9 | 5.9 | Estimated xanthine levels (normals) from Feng et al, Ther Drug Mon (2000) 22: 177-183. |
| Estimated (normals) uric acid level | 60.0 | 356.9 | Potential XO inhibitor and luminescence quenching (anti-oxidant). |
| Estimated (normals, high) uric acid level | 80.0 | 475.9 | Potential XO inhibitor and luminescence quenching (anti-oxidant). |
| Estimated uric acid highest level (gout) | 100.0 | 594.8 | Potential XO inhibitor and luminescence quenching (anti-oxidant). |

TABLE 5

Component μg/ml to μM conversion table.

| Compound | Weight mg | Volume Ml | Conc μg/ml | Conc μM |
|---|---|---|---|---|
| Adenosine | 25.0 | 1000.0 | 25.0 | 93.6 |
| Inosine | 25.0 | 1000.0 | 25.0 | 93.2 |
| Hypoxanthine | 25.0 | 1000.0 | 25.0 | 183.7 |
| Xanthine | 25.0 | 1000.0 | 25.0 | 164.4 |
| Uric Acid | 25.0 | 1000.0 | 25.0 | 148.7 |

Xanthine was found to be at a constant concentration (~6 μM) in both normal individuals and non-traumatic chest pain patient samples. It is important to discuss why a standard curve of xanthine would not be used for this assay. To prepare a standard curve of xanthine for computation of inosine and hypoxanthine concentrations would report erroneously low results, as xanthine only activates the XO enzyme once (xanthine to uric acid), whereas hypoxanthine activates the XO enzyme twice (hypoxanthine to xanthine to uric acid). Since we are only interested in inosine and hypoxanthine concentrations for this research, and with xanthine levels constant, it was appropriate to prepare hypoxanthine standards (which incorporated total inosine to hypoxanthine conversion) for this research project.

Typical spreadsheets used for luminescence experiments on inosine, xanthine, and hypoxanthine evaluations include each reagent preparation, volume pipetted into the well, and target concentrations and are listed in Tables 6, 7, and 8, respectively. Using the experimental spreadsheet for each component standard concentration range, plasma (20 μl) was pipetted into the microplate well with reagents (e.g. assay buffer, phosalin, PNP, uricase) either manually pipetted or injected using one direct injector; with the other direct injector used to inject the XO solution to start the reaction with PHOLASIN® and subsequent luminescence emission.

For Table 6: 1) Stock inosine [93.2 μM or 25 μg/ml] in DI and was prepared by adding 25 mg in 1000 mL DI (or assay buffer); 2) Working stock (WS) WS-1 (9.32 μM) 100 ul stock inosine (1:10 stock) 900 μl assay buffer; 3) Final total inosine concentration is based on 200 μl total well volume; 4) PHOLASIN® stock, conc [10 ug/ml] was prepared by adding 5 ml assay buffer to vial (50 μg PHOLASIN® from mollusca, Knight Scientific) and stored frozen; 50 μl per assay; 5) XO stock, conc [~676 mU XO/ml] was prepared by pipetting 40 μl stock (XO from bovine milk, Sigma) to 2 ml assay buffer and stored refrigerated; 40 μl per assay; 6) PNP stock, conc [~701 mU PNP/ml] was prepared by pipetting 75 μl stock (PNP from human RBC, Sigma) to 2 ml assay buffer and store refrigerated; 40 μl per assay.

For Table 7: 1) Stock xanthine [164.4 μM or 25 μg/ml] in DI. was prepared by adding 25 mg in 1000 mL DI (or assay buffer); 2) Working stock (WS) WS-1 (16.4 μM) 100 μl stock xanthine (1:10 stock) 900 μl assay buffer; 3) Final xanthine conc based on 200 μl total well volume; 4) PHOLASIN® conc [10 μg/ml] was prepared by adding 5 ml assay buffer to vial (50 μg PHOLASIN® from mollusca, Knight Scientific) and stored frozen; 50 μl per assay; 5) XO conc stock [—676 mU XO/ml] was prepared by pipetting 40 ul stock (XO from bovine milk, Sigma) to 2 ml assay buffer and stored refrigerated; 40 μl per assay.

For Table 8: 1) Stock hypoxanthine [183.7 μM or 25 μg/ml] in DI was prepared by adding 25 mg in 1000 mL DI (or assay buffer); 2) Working stock (WS) WS-1 (18.37 μM) 100 μl stock hypoxanthine (1:10 stock) 900 μl assay buffer WS-2 (1.84 μM) 100 μl WS-1 hypoxanthine (1:10 WS-1) 900 μl assay buffer; 3) Final total hypoxanthine conc based on 200 μl total well volume; 4) PHOLASIN® conc [10 μg/ml] was prepared by adding 5 ml assay buffer to vial (50 μg PHOLASIN® from mollusca, Knight Scientific) and stored frozen; 50 μl per assay; 5) XO stock, conc [~676 mU XO/ml] was prepared y pipetting 40 μl stock (XO from bovine milk, Sigma) to 2 ml assay buffer and stored refrigerated; 40 μl per assay; 6) Target range of nucleoside/purine assay (includes xanthine plus inoaine and hypoxanthine conversion to xanthine) is ~2 μM (normals) up to ~100 μM (ischemic); 7) Sensitivity and linearity of the nucleoside/purine assay (if 1:10 dilution of plasma) needs to be ~0.1 up to ~10 μM.

TABLE 6

Typical spreadsheet used for inosine luminescence experiments.

| Final Inosine Conc. [uM] | Inosine (ul) | Standard Inosine WS [uM] | Assay buffer (ul) |
|---|---|---|---|
| 0.0 | 0 | 0 | 70.0 |
| 1.0 | 21.5 | 9.32 | 48.5 |
| 2.5 | 53.6 | 9.32 | 16.4 |
| 5.0 | 10.7 | 93.2 | 59.3 |
| 10.0 | 21.5 | 93.2 | 48.5 |
| 20.0 | 42.9 | 93.2 | 27.1 |
| 30.0 | 64.4 | 93.2 | 5.6 |

TABLE 7

Typical spreadsheet used for xanthine luminescence experiments.

| Final Xanthine Conc. [uM] | Xanthine (ul) | Standard Xanthine WS [uM] | Assay buffer (ul) |
|---|---|---|---|
| 0.0  | 0    | 0     | 110.0 |
| 1.0  | 12.2 | 16.4  | 97.8  |
| 2.5  | 30.5 | 16.4  | 79.5  |
| 5.0  | 61.0 | 16.4  | 49.0  |
| 10.0 | 12.2 | 164.4 | 97.8  |
| 20.0 | 24.3 | 164.4 | 85.7  |
| 30.0 | 36.5 | 164.4 | 73.5  |

TABLE 8

Typical spreadsheet used for hypoxanthine luminescence experiments.

| Final Hypoxanthine Conc. [uM] | Hypoxanthine (ul) | Standard Hypoxanthine WS [uM] | Assay buffer (ul) |
|---|---|---|---|
| 0.0  | 0    | 0     | 110.0 |
| 0.1  | 10.9 | 1.84  | 99.1  |
| 0.2  | 21.8 | 1.84  | 88.2  |
| 0.5  | 54.4 | 1.84  | 55.6  |
| 1.0  | 10.9 | 183.7 | 99.1  |
| 2.0  | 21.8 | 183.7 | 88.2  |
| 5.0  | 5.4  | 183.7 | 104.6 |
| 10.0 | 10.9 | 183.7 | 99.1  |

Luminescence Computations

Figure 10:
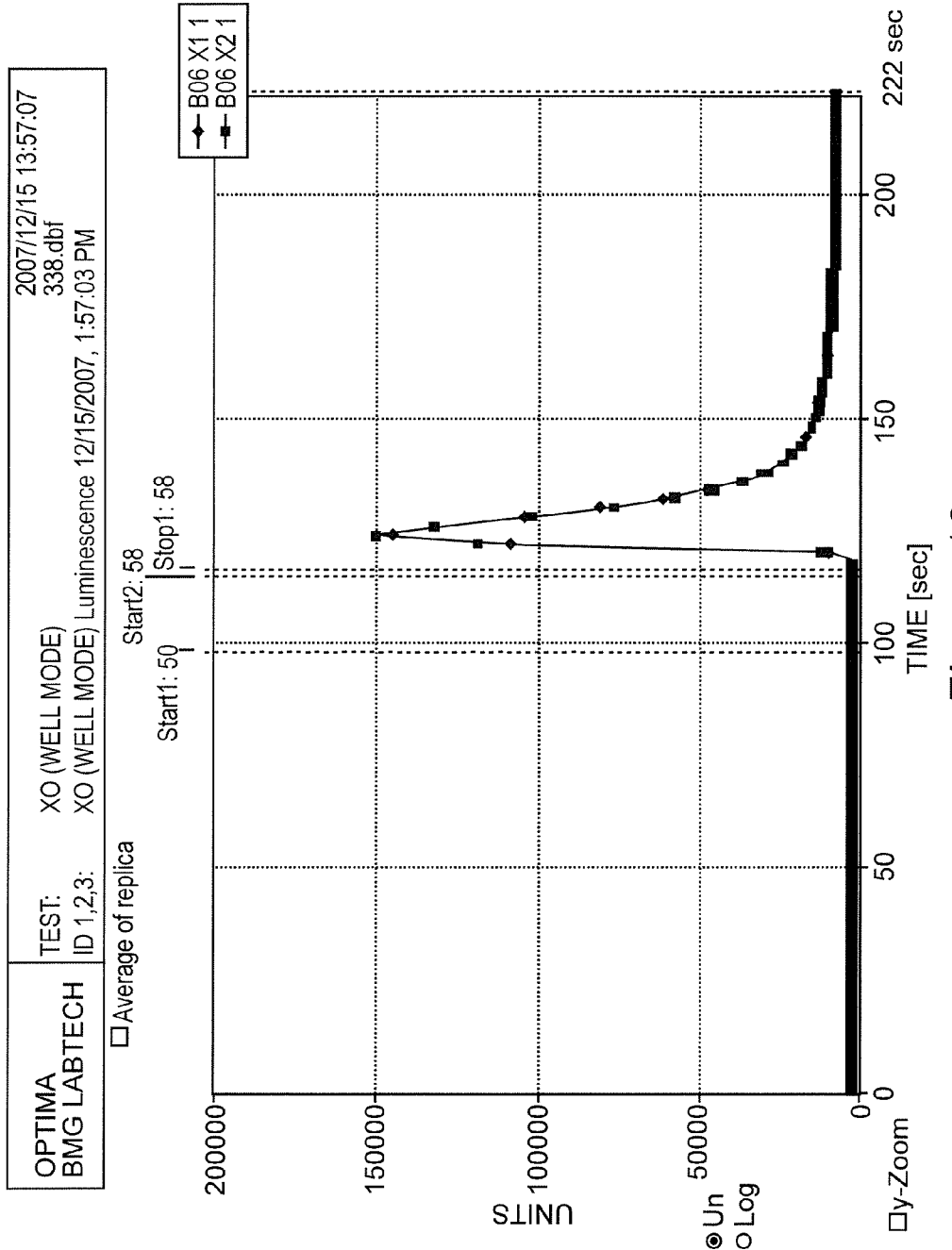
FIG. 10. Typical BMG output luminescence scan for sample analysis of 10 µM hypoxanthine in plasma. Range one (background RLU measurement between 100 and 120 sec) and range two (peak height RLU measurement between 120 sec and 222 sec).

All computations were performed using BMG Excel software with built in macros to carry out basic computations (e.g. additions, subtractions, etc.) and regression analysis (for standard curves, etc.) and data processing set points as defined by the method. FIGS. 10 and 11 represent a scan (FIG. 10, plasma with 10 μM hypoxanthine) and the RLU tabulated results (e.g. BMG Excel® Table 1, 2, and 3 in FIG. 11) from raw data acquired over the analytical run and with data acquisition set at one data point per second. The background (baseline) luminescence signal (labeled as Range 1 and presented in BMG Excel® Table 1 of FIG. 11) can be caused by reagents (e.g. buffer, PHOLASIN®, PNP, plasma) and electronic noise and was calculated as the maximum RLU signal between scan times 100-118 seconds. It would have been preferable to average the background RLU signal; however the BMG Excel® software was written to have the same computation applied to both table ranges and does not currently allow the flexibility of independent computations on each individual table.

The peak luminescence signal from the generation of light from PHOLASIN® (labeled as Range 2 and presented in BMG Excel® Table 2 of FIG. 11) and superoxide anion radicals was calculated as the maximum RLU peak height signal between scan times 119-222 seconds. BMG Excel® Table 3 (FIG. 11) represents the net RLU and is calculated by subtracting the background signal (BMG Excel® Table 1 of FIG. 11) from the peak luminescent signal (BMG Excel® Table 2, FIG. 11). The use of the peak height response of the RLU was used for the computations on these plasma samples, as some patient plasma samples RLU responses were very slow to return to background (baseline) RLU levels. The cause of the slow RLU signal return to baseline is unknown, but may be due to patient medications (e.g. vasodilators, salicylic acid) used for treatment of acute MI patients.

This luminescence method was developed to compare the RLU differences between healthy normal individual plasma samples (negative control) and samples from ED non-traumatic chest pain patients that may be experiencing acute cardiac ischemia. A comparison was made of the net RLU value between the non-traumatic chest pain patient and negative control sample, using a calculated 99% RLU reference cut-off value generated from healthy normal individuals, as the decision making RLU cut-off level. Determining the 99% RLU cut-off value is best be determined using a large number of healthy normal individuals (e.g. >>100) and calculated using the RLU mean value plus the 2.326 standard deviations (a=0.01, one tail, 99% confidence interval), and would be used to determine whether the patient has acute cardiac ischemia causing the reported chest pain. For example, if a non-traumatic chest pain patient net RLU was similar to a negative control sample net RLU, then the patient was most likely not having an acute cardiac ischemic event, but had some other type of medical condition (e.g. anxiety, heartburn) causing the reported chest pain. However, if a patient's net RLU was above the 99% RLU reference cut-off value for healthy normal individuals, then the patient was probably experiencing an acute cardiac ischemic event, and would require immediate medical attention, as it may lead to acute MI and potential adverse outcome.

Results and Discussion

Figure 12:
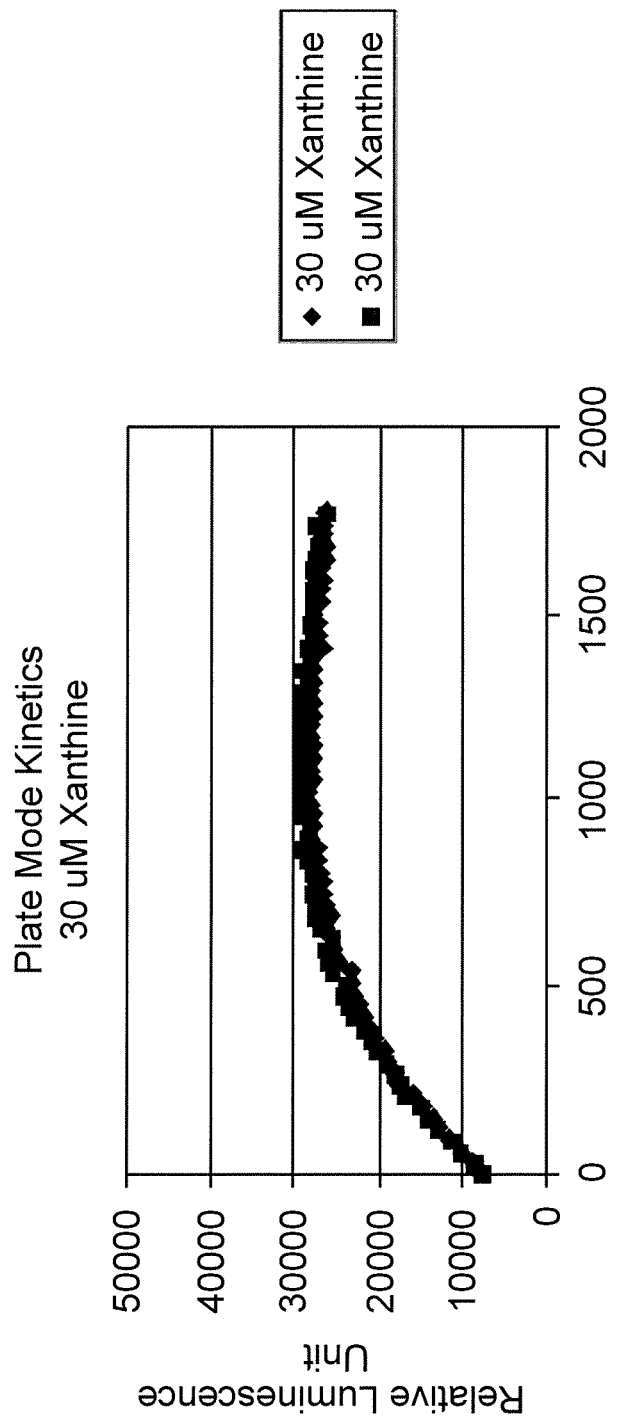
FIG. 12. Chart of relative luminescence units (RLUs) versus time (sec) for 30 µM xanthine/XO plate mode kinetics. The profile demonstrates successful equipment setup and operation using a commercial test kit for antioxidant evaluation (ABEL 61-M, Knight Scientific). Two individual samples overlay with analysis time ~30 min.

To setup the new luminometer equipment, a standardized plate mode luminescence test kit was purchased (ABEL 61M Antioxidant Test Kit, Knight Scientific, Ltd) which evaluates antioxidant capability using xanthine/xanthine oxidase and PHOLASIN®. This test kit was used to qualify the new luminometer equipment using a standardized plate mode (glow technique). However, method modifications were necessary as the plate mode analysis run time was approximately 30 min and had low sensitivity (FIG. 12) as it is developed primarily for antioxidant and glow kinetic type studies, which would be insufficient for the objective of a rapid and sensitive assay.

Figure 13:
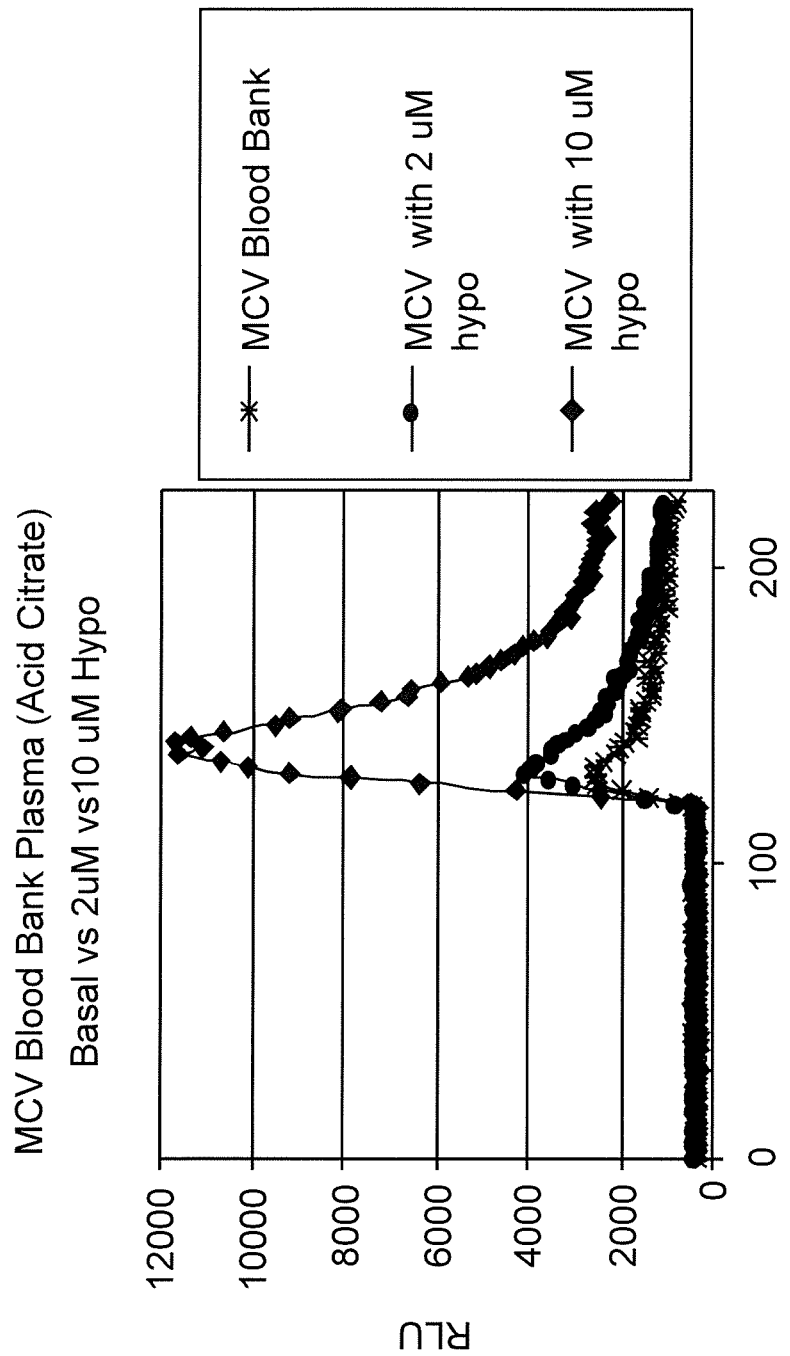
FIG. 13. Chart demonstrating a significantly reduced analysis time by utilizing increased amounts of XO (from ~10.3 mU/ml to ~676 mU/ml) and continuous microplate mixing. Analysis time ~3.7 min.

Adjustments were made to the level of XO used for analysis to increase the reaction rate (flash mode) and the incubation time of PNP enzyme for plasma inosine conversion to hypoxanthine. The starting level of XO enzyme level for the plate mode was approximately 10.25 mU/ml after reconstitution with assay buffer. With adjustment of XO to increase the concentration, the final working concentration was approximately 676 mU/ml. This resulted in an analysis time reduction from approximately 30 min to 5 min (FIG. 13). Since the commercial kit from Knight Scientific (plate mode) was set up for xanthine/xanthine oxidase analysis and studies on material antioxidant capabilities, it was necessary to increase the XO level to additionally incorporate plasma hypoxanthine levels, but more importantly to reduce the time of analysis to under 10 min (i.e. switch from glow mode to flash mode kinetics).

Figure 14A:
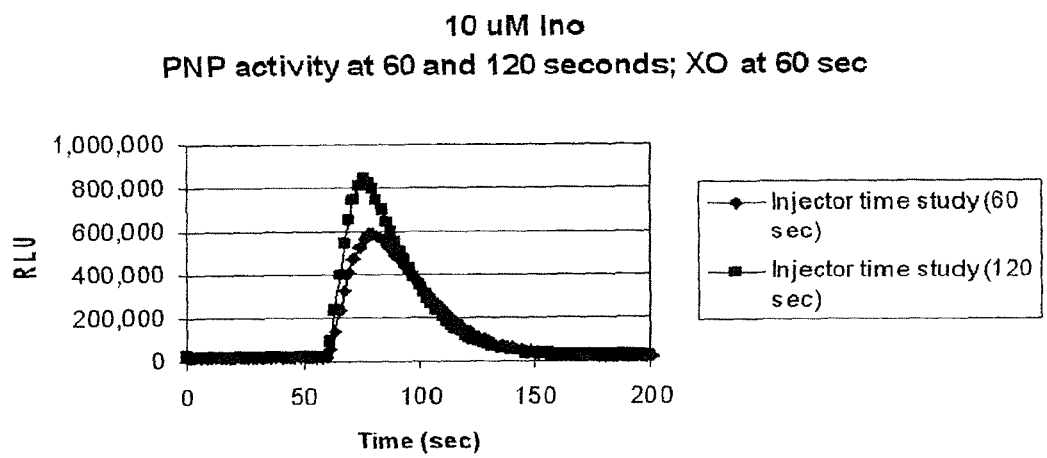
FIG. 14A-B. Charts depicting inosine and PNP incubation time and conversion study. A, evaluation of 60 and 120 sec PNP incubation times, with 120 sec demonstrating the complete conversion of inosine to hypoxanthine. B, the 10 µM inosine with PNP conversion RLU responses (n=2) overlays completely against the 10 µM hypoxanthine standard.
Figure 14B:
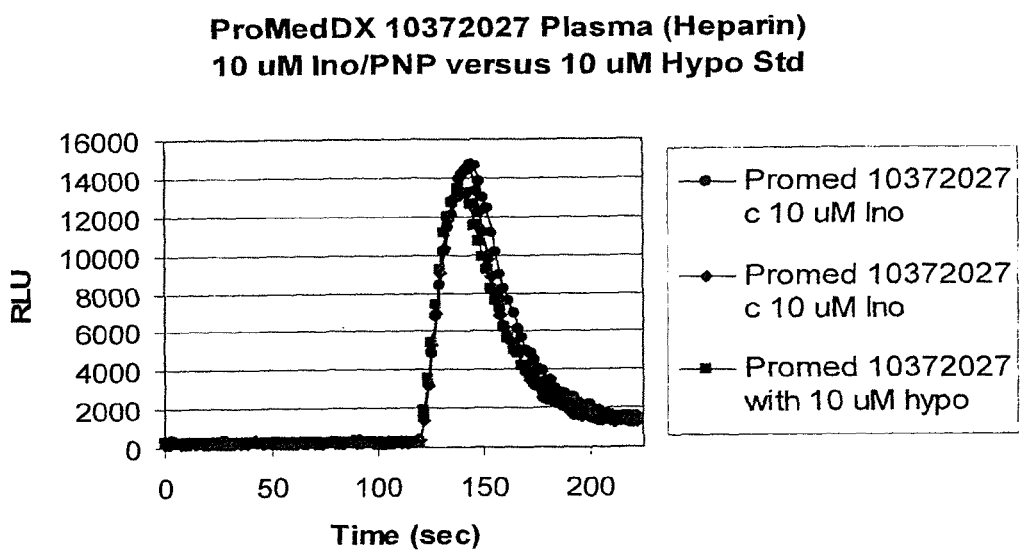

A standard curve of hypoxanthine was evaluated at concentrations from 2.3 to 30.3 μM and demonstrated sufficient linearity (normal linear regression) with correlation coefficient >0.9990 (r=2). The incubation time of purine nucleoside phosphorylase was evaluated at 60 and 120 second equilibration times using 10 μM inosine as the substrate with the monitoring of hypoxanthine level (FIGS. 14A-B). Therefore, the PNP incubation time should remain set at 120 sec to allow for complete inosine to hypoxanthine conversion, with subsequent XO injection to start the luminescence reaction. In some embodiments, in order to reduce the overall analysis time, the PNP enzyme is added to the sample collection tube (e.g. BD vacuutainer), with inosine conversion then occurring during the whole blood to plasma centrifugation step, eliminating the need for a 120 sec PNP incubation time; and reducing the analysis time to only 30 seconds (assumes injection of XO at 0.1 sec and measurement of peak height RLU response).

Figure 15A:
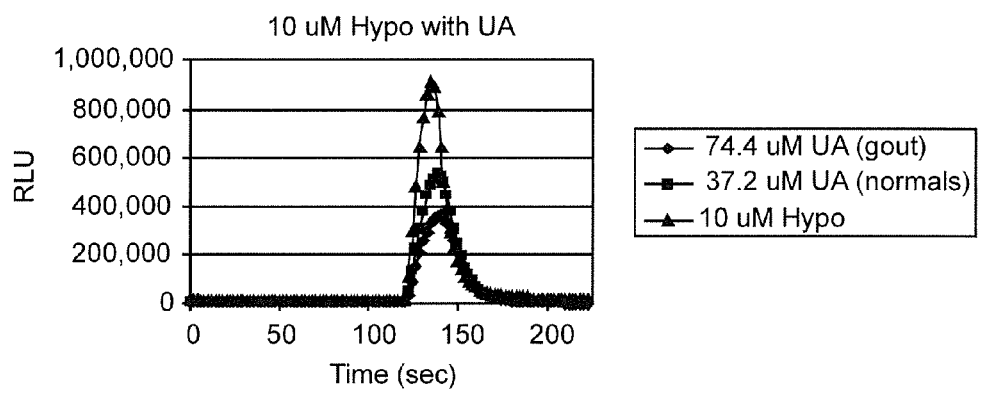
FIG. 15A-B. Charts demonstrating effects of uric acid (human physiological levels) on PHOLASIN® luminescence signal. A, high levels of uric acid (in buffer) can quench the luminescence by more than 50%. B, treatment of plasma (1:100 dilution) and use of strong anion exchange (SAX) can reduce antioxidant effect on the luminescence signal and increase method sensitivity.
Figure 15B:
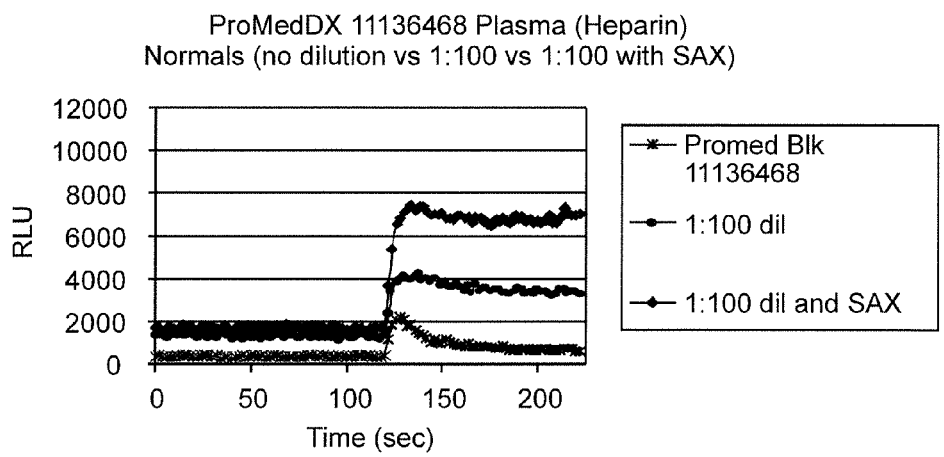

A study of the effect of plasma uric acid on luminescence response was performed. Since uric acid is found in plasma at relatively higher concentrations (normal range ~350-475 µM) and is a known antioxidant, it was important to evaluate its potential effect on the luminescence signal. As seen in FIG. 15A, the uric acid's antioxidant affects decreases the luminescence signal (~50% quenching). To address the uric acid, an experiment was performed using strong anion exchange (SAX) resin to remove organic anions from the plasma matrix. Also seen in FIG. 13B is a 1:100 dilution of plasma and subsequent use of the SAX pipet tip (Varian, Inc, CA, USA); both demonstrated that removal of potential interfering organic acids (e.g. urate at pH 7.4) resulted with an increase in luminescence response and sensitivity. Since the blank plasma used had approximately 500 nM hypoxanthine, the 1:100 dilution using deionized water and subsequent use of SAX sorbent makes detection levels of hypoxanthine at the pM levels attainable.

Figure 16:
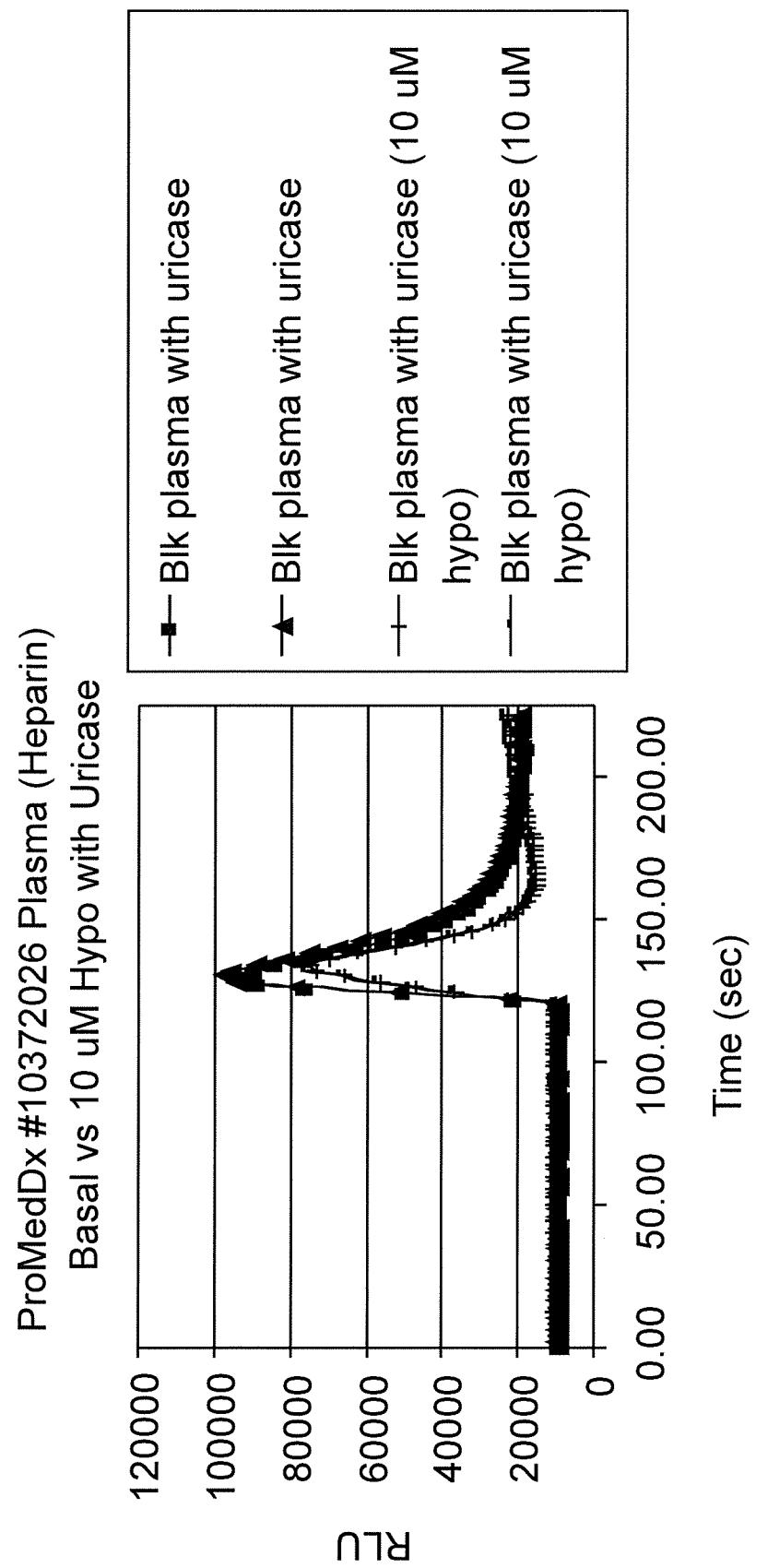
FIG. 16. Chart demonstrating the effect of uricase on basal uric acid levels (normal healthy individual) and with fortification of 10 µM hypoxanthine. The generation of hydrogen peroxide (by-product) from uricase enzymatic conversion of uric acid to allantoin caused XO inactivity (potentially from hydrogen peroxide product inhibition on XO effect).
Figure 17A:
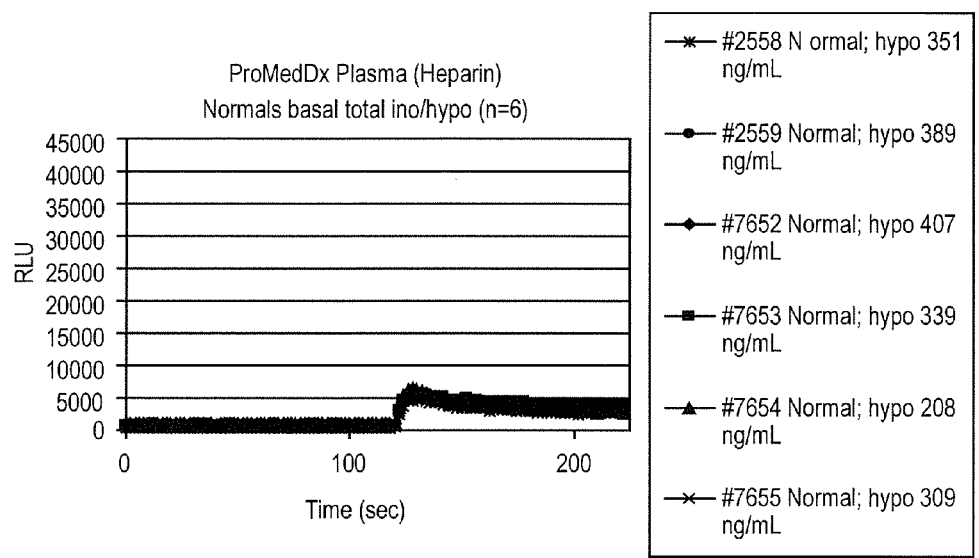
FIG. 17A-B. Charts demonstrating healthy normal individuals and patients with confirmed acute MI (hospital documented elevated levels of cTnT). A, all cTnT patient samples RLU response were clearly above the calculated 99% cut-off reference value (5,944 RLU) for healthy normal individuals (n=6 for each group). B, HPLC values for total hypoxanthine and cTnT values (from ProMedDx) are listed in the legend.
Figure 17B:
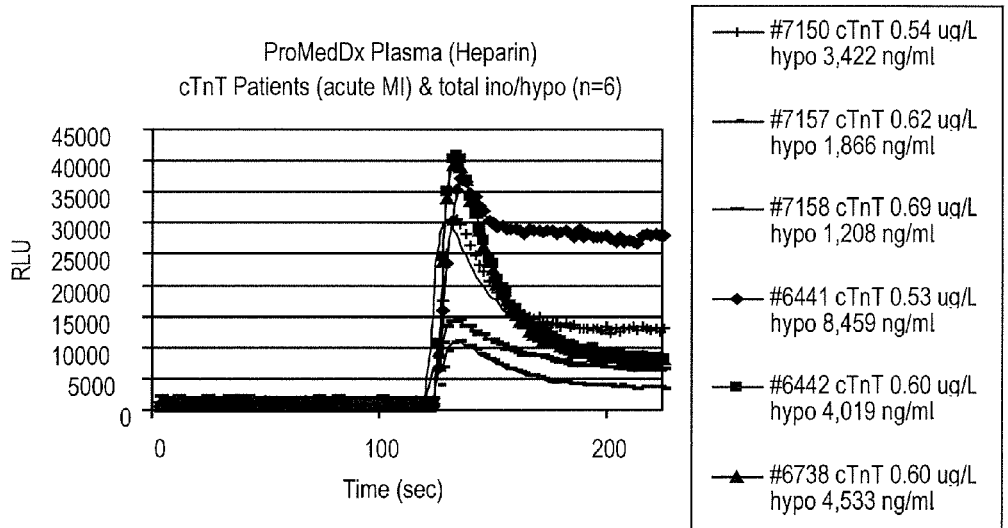
Figures 18A, 18B:
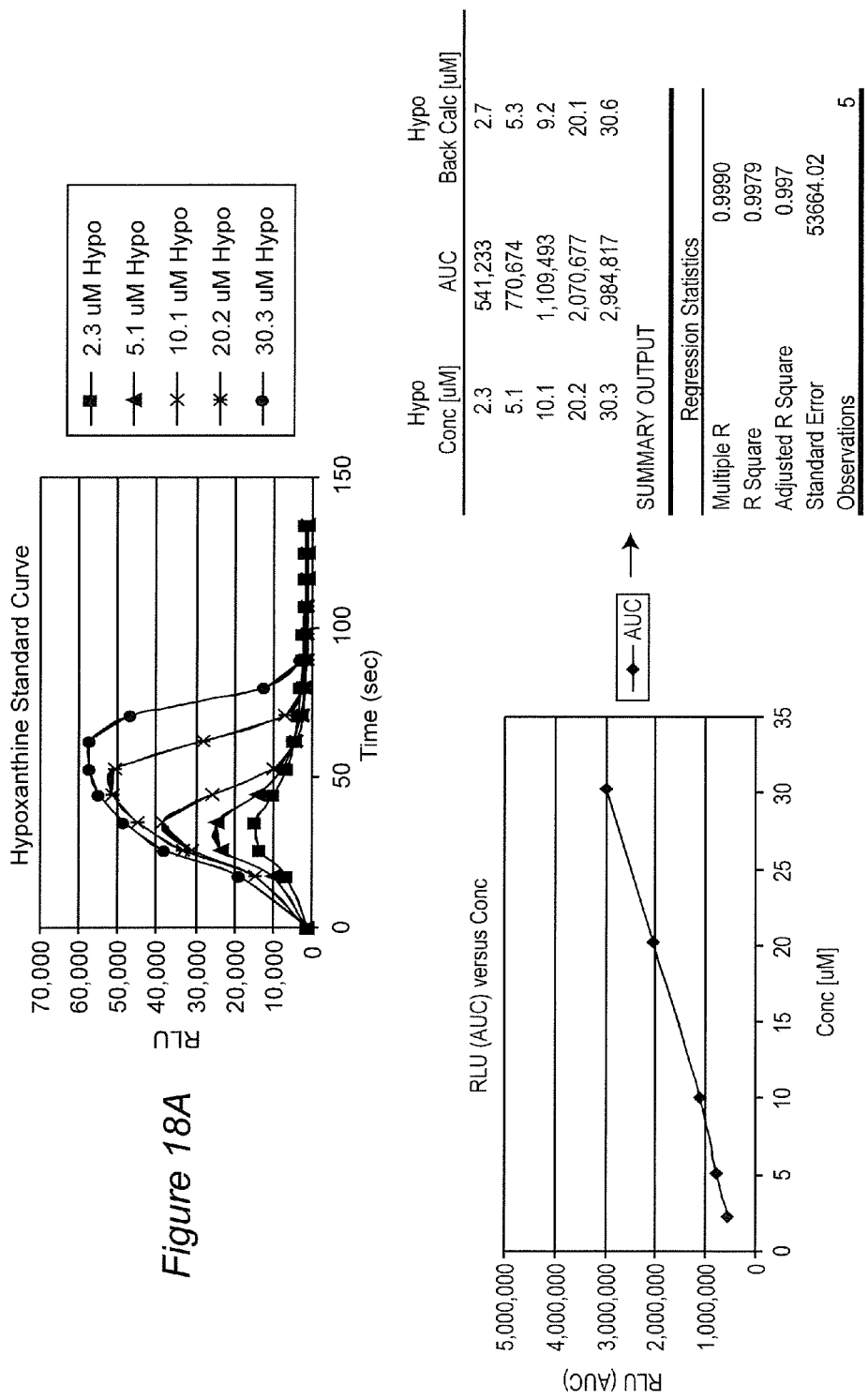
FIG. 18A-B. A, hypoxanthine standard curve in assay buffer ranging from 2.3 to 30.3 µM demonstrating sufficient linearity and B, back-calculated hypoxanthine concentrations.
Figure 19A:
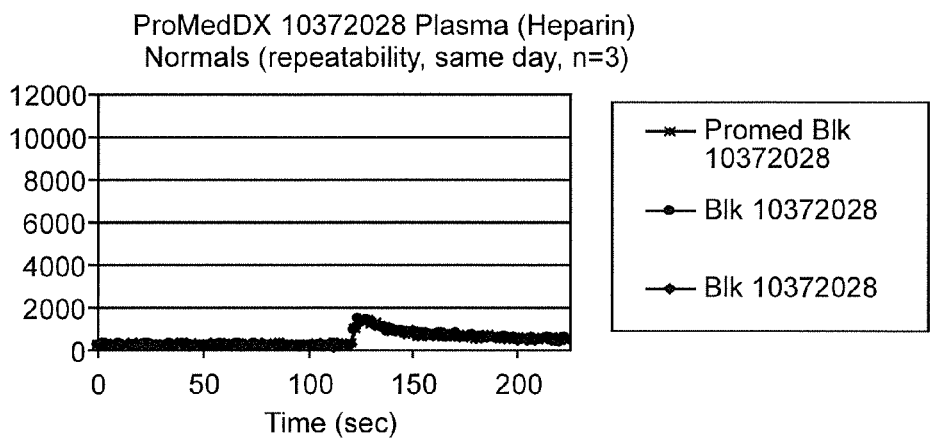
FIG. 19A-B. Charts demonstrating repeatability of the luminescence assay. Healthy normal individual (basal level, ~0.5 µM hypoxanthine) and fortified sample (1.5 µM hypoxanthine) assayed three consecutive times. Overlay of profiles demonstrate plasma sample repeatability.
Figure 19B:
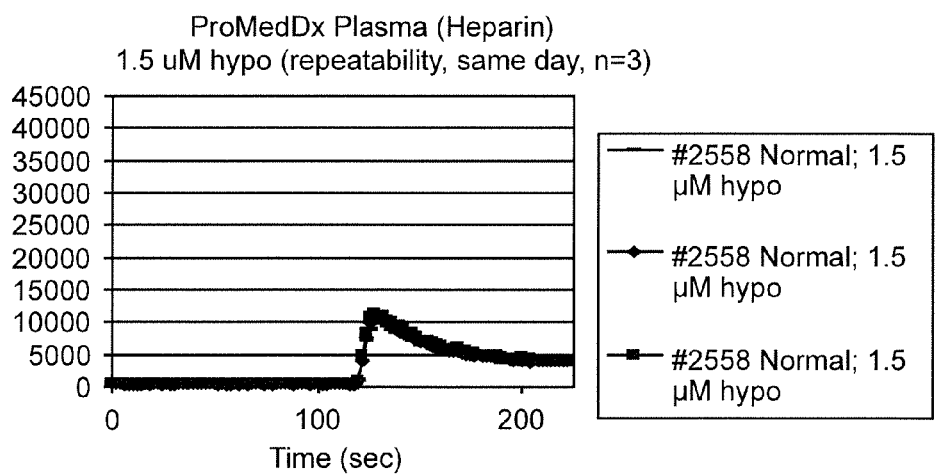

A second approach to eliminate the uric acid was to utilize uricase (~1.1 U/ml from *Arthrobacter globiformis* bacteria, Sigma, USA) during the PNP incubation time in an attempt to eliminate the endogenous uric acid. As seen in FIG. 16, it appears that the XO enzyme is deactivated (product inhibition) by the presence of large amounts of by-product hydrogen peroxide that is generated by uricase activity. As one by-product of XO activity is the production of hydrogen peroxide, this finding was not completely surprising due to the effects of product inhibition on XO enzyme turnover. One possible solution to eliminate the generated hydrogen peroxide is to use horseradish peroxidase, which catalyzes hydrogen peroxide to products water and oxygen, but this additional enzyme would only add to the complexity and cost of the analysis and therefore not evaluated. However, the use of the both uricase and SAX pipet tip technology to eliminate organic acids (e.g. uric acid) was probably not necessary to use, as differences in luminescence response between the healthy normal individuals and confirmed acute MI patients (elevated cTnT levels) was significant (t-test, a=0.05, p<0.01), when using the 99% percentile (a=0.01, one tail, 2.326 standard deviations for n=6) as the calculated biomarker cut-off reference value for acute cardiac ischemia (FIG. 17). Even though this research utilized a small sample set for evaluation (n=6 for each group), the 99% cut-off for healthy normal individuals was 5,946 RLU, with all six cTnT patients clearly above this calculated decision point cut-off RLU level. The luminescence method was optimized for rapid evaluation of hypoxanthine in plasma to potentially be used in an ED clinical type environment. For this research study, method parameters such as calibration, repeatability and limit of detection were evaluated using hypoxanthine standards. The method demonstrated linearity from 2.3-30.3 µM hypoxanthine in assay buffer (R=0.9990, n=2) (FIG. 18). This range covered the low and midpoint total hypoxanthine concentrations of samples from HPLC analysis of healthy individuals and non-traumatic chest pain patients, and focused on the potential biomarker cut-off concentration for this small group of samples (n=20). Repeatability (n=3) was evaluated by fortification of plasma at basal (~0.5 µM) and 1.5 µM hypoxanthine concentrations (final well levels) and demonstrated by consistent RLU overlays (FIG. 19A-B).

Conclusion

A rapid luminescence method was developed for the detection of inosine and hypoxanthine in human plasma. Using only 20 ul of plasma (heparin) and instrument direct injectors, the method allowed for the rapid (<5 min) detection of total hypoxanthine (as inosine is converted to hypoxanthine using enzyme PNP) concentrations, which may be used as a biomarker of acute cardiac ischemia. The use of a hypothetical cut-off level (e.g. 99% confidence) relative luminescence unit (RLU) for decision making (i.e. positive level, negative level) may be the most effective use of this rapid screening assay. The method was utilized for evaluation of plasma samples from healthy individuals and cardiac patients with confirmed acute myocardial infarction (hospital documented elevated plasma cTnT levels), and demonstrated the potential of this rapid assay to be used as a diagnostic tool, for use by emergency department services personnel on non-traumatic chest pain patients suspected of undergoing acute cardiac ischemia.

Example 4

Use of the Assay of the Invention in the Evaluation of Patients with Chest Pain and the Diagnosis or Ruling Out of a Cardiac Ischemic Event In the United States alone, approximately 8 million patients are evaluated in emergency rooms due to non-traumatic chest pain. It is estimated that about 2-5% of these patients are actually experiencing acute myocardial infarction, but are mis-diagnosed and discharged. This could be, for example, about 400,000 people annually that are incorrectly diagnosed and discharged without proper therapy. Worldwide, the numbers are even more daunting.

Possible other conditions that may cause chest pain include gastroesophageal reflux, acid reflux, various musculoskeletal spasms, pneumonia, aortic dissection, nerve impingement, pulmonary emboli, spontaneous pneumothorax, acute pericarditis, heartburn, asthma, anxiety and ulcers. Typical testing for diagnosing acute MI includes noting patient's vital signs, symptoms and history; an electrocardiogram (ECG) which measures heart electrical activity; a blood analysis, which is limited to detecting indicators of heat tissue necrosis (e.g. cardiac troponin I and T, myoglobin, creatine kinase); an echocardiogram, which can show both false positive and false negative results, up to about 20%; and stress testing (e.g. on a treadmill), which is rarely done. The primary goal of an emergency department is to rule-in myocardial infarction, which requires immediate treatment. The World Health Organization recommends that 2 out of 3 possible indicators be positive in order to diagnose probably MI. Ruling out MI, however, is extremely difficult and using the technology available prior to the present invention, could take several days. As many as ⅓ of patients have few or no classical symptoms. Significantly, a majority of acute myocardial infarction (AMI) deaths occur within a 12-hour window of onset but cannot be prevented without proper diagnosis.

FIG. 20 is a flow chart of a typical ER triage of a patient presenting with chest pain. However, this chart includes the detection of the early biomakers inosine and hypoxanthine, using the rapid luminescence test described herein. Using the method, within minutes of obtaining a blood sample, an accurate indicator of cardiac ischemia can be obtained. If levels of inosine and/or hypoxanthine are elevated (e.g. confidence level of 99% or greater), then an assumption of early cardiac ischemia can be made and appropriate treatment to prevent AMI can be instigated immediately, particularly if one other test is also positive. Thereafter, the test may be run again as necessary or advisable, e.g. to confirm that intervention has succeeded, to test for a possible second AMI, etc. Even if the test is negative, a repeat assay after a relatively short time period of observation (e.g. about 1-3 hours), and thereafter as deemed necessary, can be carried out to confirm that indeed an AMI is not likely to be imminent, and another cause of the chest pain should be explored. Thus, the percentage of patients who are misdiagnosed and discharged without appropriate treatment is minimized.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of diagnosing an acute ischemic event in a human subject, comprising the steps of
    adding xanthine oxidase (XO) enzyme to a biological sample obtained from said human subject;
    measuring metabolic byproducts of enzymatic activity of XO enzyme on xanthine and hypoxanthine in said biological sample using a luminometer; and
    determining whether or not said patient is experiencing an acute ischemic event based on a measurement made in said measuring step.

2. The method of claim 1 wherein said steps of adding, measuring, and determining are performed in 10 minutes or less.

3. The method of claim 1, wherein said steps of adding, measuring, and determining are performed in 1 minute or less.

4. The method of claim 1 wherein said metabolic byproducts are selected from the group consisting of hydrogen peroxide, superoxide anion radicals (SAR), and hydroxyl free radicals.

5. The method of claim 1 wherein said measuring step includes the step of using a chemiluminescent agent in said biological sample when measuring said metabolic byproducts.

6. The method of claim 5, wherein signal enhancers are used together with said chemiluminescent agent.

7. The method of claim 1 wherein said measuring step includes using a substrate to which said XO enzyme is bound or associated.

8. The method of claim 6 wherein said substrate is selected from the group consisting of a test strip and a bead.

9. The method of claim 1 further comprising the step of decreasing the antioxidant effect of uric acid in said biological sample to increase sensitivity during said measuring step.

10. The method of claim 1 further comprising the step of diluting said biological sample prior to said measuring step.

11. The method of claim 10 wherein said step of diluting includes the step of using a diluent which buffers said biological sample between pH 7.2 and pH 7.8.

12. The method of claim 1, further comprising the step of adding purine nucleoside phosphorylase (PNP) to said sample prior to said step of adding XO.

13. The method of claim 1, wherein said biological sample is selected from the group consisting of blood, plasma, saliva, spinal fluid, and urine.

14. The method of claim 1 wherein said acute ischemic event is a stroke.

* * * * *